(12) United States Patent
Knight et al.

(10) Patent No.: US 11,458,185 B2
(45) Date of Patent: Oct. 4, 2022

(54) ANTIOXIDANT DIETARY SUPPLEMENT COMPOSITIONS

(71) Applicants: ABEL APPLICATIONS LIMITED, Plymouth (GB); NATURALIFE HEALTH UNLIMITED COMPANY, Rathnew (IE)

(72) Inventors: Jan Knight, Plymouth (GB); Darragh Hammond, Rathnew (IE)

(73) Assignees: Abel Applications Limited, Plymouth (GB); Naturalife Health Unlimited Company, Rathnew (IE)

( * ) Notice: Subject to any disclaimer, the term of this patent is extended or adjusted under 35 U.S.C. 154(b) by 0 days.

(21) Appl. No.: 16/612,483

(22) PCT Filed: May 11, 2018

(86) PCT No.: PCT/GB2018/051290
§ 371 (c)(1),
(2) Date: Nov. 11, 2019

(87) PCT Pub. No.: WO2018/206985
PCT Pub. Date: Nov. 15, 2018

(65) Prior Publication Data
US 2020/0061145 A1 Feb. 27, 2020

(30) Foreign Application Priority Data
May 12, 2017 (GB) .................... 1707672

(51) Int. Cl.
| | |
|---|---|
| *A61K 36/00* | (2006.01) |
| *A61K 36/87* | (2006.01) |
| *A23L 33/105* | (2016.01) |
| *A23L 33/15* | (2016.01) |
| *A61P 11/00* | (2006.01) |
| *A61K 36/15* | (2006.01) |
| *A61K 36/82* | (2006.01) |

(52) U.S. Cl.
CPC ............ *A61K 36/87* (2013.01); *A23L 33/105* (2016.08); *A23L 33/15* (2016.08); *A61K 36/15* (2013.01); *A61K 36/82* (2013.01); *A61P 11/00* (2018.01); *A61K 2300/00* (2013.01)

(58) Field of Classification Search
CPC ...................................... A61K 36/00
USPC ........................................ 424/725
See application file for complete search history.

(56) References Cited

U.S. PATENT DOCUMENTS

| | | | |
|---|---|---|---|
| 8,361,520 B2 | 1/2013 | Palmer | |
| 9,180,077 B2 | 11/2015 | Lambelet et al. | |
| 2003/0086986 A1 | 5/2003 | Bruijn et al. | |
| 2009/0110789 A1 | 4/2009 | Mower et al. | |

FOREIGN PATENT DOCUMENTS

| | | |
|---|---|---|
| EP | 2263481 A1 | 12/2010 |
| KR | 20120132758 A | 12/2012 |

OTHER PUBLICATIONS

European Patent Office, International Search Report, issued in PCt/GB2018/051290, dated Jul. 24, 2018, 4 pages, European Patent Office, Rijswijk, Netherlands.

Hossam S. El-Beltagi et al, Synergistic Antioxidant Scavenging Activities of Grape Seed and Green Tea Extracts against Oxidative Stress, Notulae Botanicae Horti Agrobotanici CluJ-Napoca, pp. 367-374, vol. 44, No. 2, Dec. 14, 2016, Not Bot Horti Agrobo, XP055494581.

*Primary Examiner* — Michael V Meller
(74) *Attorney, Agent, or Firm* — Marshall & Melhorn, LLC

(57) ABSTRACT

An antioxidant dietary supplement composition comprises from 37 to 42% by weight of grapeseed extract, from 32 to 37% by weight of green tea extract, from 7 to 15% by weight of pine bark extract and from 7 to 15% by weight of pomegranate extract, wherein the % by weight is based on the total weight of the grapeseed extract, green tea extract, pine bark extract and pomegranate extract in the composition. The composition has use in the treatment of viral infections, especially respiratory infections, in mammals and birds, especially in humans, horses and camels. Also disclosed is a method of treating a viral infection in a mammal or bird which comprises administering to the mammal or bird a composition according to the invention.

3 Claims, 22 Drawing Sheets

ANTIOXIDANT DIETARY SUPPLEMENT COMPOSITIONS

The present invention relates to an antioxidant dietary supplement composition. More specifically, it relates to compositions comprising grapeseed extract and green tea extract. The compositions have use in the treatment of respiratory infections, such as colds and influenza, in mammals. The present invention provides an antioxidant dietary supplement composition comprising grapeseed extract and green tea extract, wherein the grapeseed extract is present in the composition in an amount of from 40% to 60% by weight based on the total weight of the grapeseed extract and green tea extract and the green tea extract is present in the composition in an amount of from 60% to 40% by weight based on the total weight of the grapeseed extract and green tea extract.

Grapeseed extract and green tea extract are known dietary supplements. Grapeseed extract is an industrial derivative of grapeseeds, extremely rich in antioxidants and oligomeric proanthocyanidin complexes, typically ≥95% proanthocyanidins, and has been linked to a wide range of possible therapeutic properties. The material is easily available commercially and typically is provided in the form of a fine, red-brown powder. It is obtained commercially by extraction, using water and ethanol, from the seed of *Vitis vinifera* L. It has been suggested that grapeseed extract may be beneficial in the treatment of conditions such as high cholesterol, atherosclerosis, macular degeneration, poor circulation and nerve damage. Green tea extract is also an easily available material and is provided as a fine, yellow-brown powder. It is obtained commercially from the leaves of *Camellia sinensis* by extraction using alcoholic solutions. Green tea extract has been used in traditional Chinese medicine for centuries to treat a wide variety of medical conditions, from headaches to depression. Green tea extract is known to contain high levels of polyphenols such as flavanols, flavandiols and flavonoids. Green tea extract typically contains ≥95% polyphenols. Polyphenols contained in green tea include six primary catechin compounds: catechin, gallocatechin, epicatechin, epigallocatechin, epicatechin gallate and epigallocatechin gallate (also known as EGCG).

While the antioxidant effects of grapeseed extract and green tea extract are known, we have found that when these two substances are combined in the amounts disclosed above, the resulting antioxidant activity of the mixture is greater than the sum of the individual activities of grapeseed extract and green tea extract. Thus, we have discovered that the grapeseed extract and the green tea extract appear to interact in admixture in certain proportions such that a synergistic effect is achieved in the antioxidant activity of the mixture.

In addition to the synergistic effect mentioned above, we have additionally found that further synergy occurs when the composition additionally contains at least one of pine bark extract, and pomegranate extract. Pine bark extract is easily available commercially as a fine, brownish-yellow powder. It is known to contain ≥95% oligopolymeric proanthocyanidins (OPC). Pomegranate extract, commercially available as a fine light grey or brown powder, is known to contain 40 to 90% Elagic acid. It is obtained from the seeds of *Punica granatum*. Preferably, the composition contains both pine bark extract and pomegranate extract.

Thus, according to a preferred embodiment of the invention, the composition comprises from 30 to 45% by weight of grapeseed extract, from 30 to 45% by weight of green tea extract, from 5 to 20% by weight of pine bark extract and from 5 to 20% by weight of pomegranate extract, wherein the % by weight is based on the total weight of the grapeseed extract, green tea extract, pine bark extract and pomegranate extract in the composition. More preferably, the composition comprises from 35 to 45% by weight of grapeseed extract, from 30 to 40% by weight of green tea extract, from 5 to 15% by weight of pine bark extract and from 5 to 15% by weight of pomegranate extract, wherein the % by weight is based on the total weight of the grapeseed extract, green tea extract, pine bark extract and pomegranate extract in the composition. Most preferably, the composition comprises from 37 to 42% by weight of grapeseed extract, from 32 to 37% by weight of green tea extract, from 7 to 15% by weight of pine bark extract and from 7 to 15% by weight of pomegranate extract, wherein the % by weight is based on the total weight of the grapeseed extract, green tea extract, pine bark extract and pomegranate extract in the composition.

The compositions of the invention may also contain additional ingredients, for example, one or more fillers. Examples of fillers include rice flour, vitamin C, Echinacea, elderberry extract, elderflower extract, and extracts of berries of the genera *Ribes* and *Rubus*, such as blackcurrant (*Ribus nigrum*), blackberry (*Rubus fruticosus*), raspberries (*Ribus idaeus*) and redcurrants (*Ribus rubrum*).

The composition of the invention has particular use in the treatment of viral infections in mammals, including humans, and in birds, especially respiratory infections such as colds and influenza. We, also, believe the composition is effective in the treatment of shingles in humans since we have received anecdotal reports of humans, taking the composition, recovering rapidly from shingles. We, further, believe that the composition has use in the treatment of camels infected by Camel Pox, a viral skin condition caused by the Camel pox virus which is closely related to Variola virus, the causative agent of smallpox.

The invention, further, provides a method of treating a viral infection in a mammal or a bird, especially a respiratory infection, which comprises administering to the mammal or bird a composition according to the invention, as described above. The method is useful for treating humans. It can, however, also be used to treat non-human mammals and birds. Examples of non-human mammals include horses, camels, dogs and cats. Examples of birds include chickens and other poultry birds.

A particular advantage of the present invention is that it provides an opportunity to treat an infection without resorting, initially, to the use of antibiotics. If an infection appears to be viral, although this is not confirmed, the composition of the invention may be taken by, or administered to, the sufferer of the infection. If, after 24 hours, there is no improvement, judged by the way the sufferer feels and/or by a light emission curve produced using a blood sample, then the administration of an antibiotic may be considered. Since light emission curves, when an infection is bacterial, have a distinct shape, it is possible to decide to use an antibiotic if an infection does not respond to the composition of the invention. Furthermore, if an antibiotic is used and the light emission curve shows no response to the antibiotic used, it is possible to recommend treatment of a patient using a different antibiotic. The present invention, therefore, makes it possible to avoid the use of unnecessary antibiotics.

A dose, for a human, is typically 400-500 mg. This, typically, will be administered orally, via a capsule or tablet. The composition can, however, be administered as an aqueous suspension. The dosage, for administration to a horse, is typically about 5 times that used for humans. A similar dosage may be used to treat a camel. However, since camels are pseudo-ruminants, it is important to avoid the dose, in liquid form, reaching the stomach of a camel. Preferably, when treating a camel, the composition is delivered by way of a syringe into the mouth, carefully delivering it onto the mucosa lining at the back of the mouth so that it is absorbed directly into the blood. For the treatment of dogs, cats and other small mammals, the delivery can be either on/in the food or in a liquid form as used for horses and camels. The dose will, of course, vary depending on the mass of the animal. For chickens and other birds, the composition can be delivered in the feed and/or in drink.

We have previously found that the presence of an infection agent in a human body can be detected, even pre-symptomatically, by contacting leucocytes derived from the human body with a luminescence reagent which emits light on reaction with an oxidant, adding an activator to the mixture of leucocytes and the luminescence reagent and then continuously monitoring and/or measuring light emitted. This method provides a way of monitoring the effects of the composition of the invention in the body after it has been administered.

Thus, the monitoring of the effects of the composition can be carried out by a method comprising:
a) contacting leucocytes in, or obtained from, a blood sample provided by an individual with a luminescence reagent which emits light on reaction with an oxidant;
b) adding an activator to the mixture of leucocytes and luminescence reagent;
c) continuously monitoring and/or measuring light emitted by the luminescence reagent over a predetermined time period commencing before and ending after the addition of the activator; and
d) assessing the light emission to determine the presence of the infection agent.

The method is carried out on leucocytes contained in, or obtained from a blood sample taken from the individual under test. The test can be carried out using whole blood (optionally diluted) or on a leucocyte-containing isolate, such as isolated leucocyte cells. Methods of isolating leucocytes from whole blood are, of course, well known. Only a small sample is required for testing in the method, such as provided from a pin prick rendered to the individual.

According to the method, the blood sample, typically diluted, or a sample of leucocytes isolated from whole blood, is contacted with a luminescence reagent which emits light on reaction with an oxidant. Such luminescence reagents, generally, are well known in the art and examples include lucigenin, luminol (3-aminophthalhydrazide, 5-amino-2,3-dihydro-1,4-phthalazinedone), isoluminol (4-aminophthalhydrazide), MCLA (5-(methoxyphenyl)-2-methyl-3, 7-dihydroimadazol [1,2-a] pyrazine-3 (7H)-one hydrochloride and PHOLASIN™ (PHOLASIN is a registered trade mark of Knight Scientific Limited) which is the photoprotein derived from the marine bivalve mollusc *Pholas dactylus*. PHOLASIN™ is preferred for use in the method in view of its ultrasensitivity towards free radicals such as the superoxide anion and other reactive oxygen-containing species (ROS) as well as its ability to react with enzymes such as peroxidases. It is also possible to use a synthetic equivalent of the photoprotein derived from *Pholas dactylus*.

An activator is added to the mixture of leucocytes and luminescence reagent to stimulate the NADPH oxidase system of the leucocytes. Through this stimulation, free radicals and/or reactive oxygen species produced excite the luminescence reagent resulting in the emission of light by the reagent. Examples of activators that may be used include the receptor stimulant N-formyl-methionyl-leucyl-phenylalanine (fMLP) and the phorbol ester, Phorbol-12-myristate-13-acetate (PMA) which enters the cell and activates protein kinase C directly. Presentation of fMLP and PMA together enables the activation of the NADPH oxidase on the cell surface to be monitored simultaneously with the activation of the NADPH oxidase on the membrane of secondary granules. PMA activates the NADPH oxidase throughout the cell, but at a slower rate than fMLP and it also promotes degranulation. In addition, platelet activating factor (PAF), which binds to fMLP receptors and also enters the cell, can also be used since it acts in a similar way to using a combination of fMLP and PMA. Other mediators, such as anti-Fc receptor antibodies and lipopolysaccharides (LPS) may also be used in concentrations that either prime the cell to respond to fMLP or PAF or that actually stimulate the production of free radicals and release of enzyme-containing granules.

According to the method, light that is emitted by the luminescence reagent is monitored and/or measured over a predetermined time period which commences before the addition of the activator to the mixture of luminescence reagent and leucocytes and which ends after the addition of the activator. The light emitted will typically be monitored and/or measured by the use of a luminometer. In the case of the luminescence reagent PHOLASIN™, a low level light, known as the resting glow, is emitted before the leucocytes are activated but, on the addition of the activator, light emission is increased to a level determined by the degree of stimulation of the leucocytes and the light emitted over the time period of the observation changes with time elapsed since the addition of the activator. Thus, over the predetermined time period during which light emission is monitored and/or measured, the effect of the addition of the activator to the leucocyte/luminescence reagent mixture, i.e. the level of response of the leucocytes, is seen. The predetermined time period will be chosen depending on the type of activator, i.e. whether it activates the leucocyte by binding to cell surface receptors such as occurs with fMLP or by activating within the cell membrane (i.e. PMA) or a combination such as occurs with platelet activating factor. Concentration of leucocytes and/or luminescence reagent in the test solution will determine the length of time to carry out the assay as well as the kind of luminometer used. Assays performed in microplate luminometers generator take longer to complete than assays performed on single samples in tube luminometer. The measuring time is typically less than 30 minutes, preferably less than 20 and more preferably less than 15 minutes. It is also possible to standardise the method and get faster assays which generally run for 5 minutes after presentation of the activator.

The emission of light by the luminescence reagent is preferably recorded with respect to time over the predetermined period of time. Through our research we have found, surprisingly and unexpectedly, that a plot of emitted light intensity against time produces a light emission curve which, in the case of an individual infected by an infection agent, is characteristically different from a control light emission curve produced using leucocytes taken from a normal, fit, healthy individual. We have found, for instance, that the peak intensity of emitted light recorded after the addition of the activator to the mixture of leucocytes and luminescence reagent and/or the overall shape of the light emission curve, compared to a control light emission curve, may be indicative of one or more problems in the health and wellbeing of the individual under test. A control, light emission curve produced using leucocytes obtained from a blood sample taken from a normal, fit and healthy individual has a shape characterised by an immediate and steep rise in light emission, following the addition of the activator, to reach a peak, which peak is followed by a significant tailing off of light emission with time elapsed from the peak value, gradually returning to low light emission within a few minutes. We have also been able to produce a reference curve made up of the mean response curves of 385 individuals±1 standard deviation (sd) with such a 'normal' shaped curve. The magnitude of this reference curve above and beneath the mean curve defines the range of luminescent response of someone feeling very good.

Compared to the control or reference curve, a curve produced using leucocytes obtained from a blood sample taken from an individual who is infected by an infection agent, whether or not the individual has experienced any symptoms of the infection at the time the blood sample is taken, shows an excessive response characterised by a peak light emission value higher than that of the control. When the peak, of magnitude significantly higher than the upper limit of the reference range, occurs rapidly after stimulation with the receptor stimulant fMLP, the infective agent to which the leucocyte is responding is usually a virus. As the infection proceeds, the general shape of the curve becomes a little more rounded compared to the curve obtained in the early stages of the infection. However, this rounding of the curve resulting from exposure of the leucocytes to a virus should not be confused with an extremely rounded curve with a much later time to peak and a significantly greater area under the curve. This much rounder curve with a later time to peak has been confirmed, indirectly, to be due to a bacterium as the individual with this shaped curve responded to treatment with antibiotics and expressed feeling much better as well as the blood tested corresponded with a decreasing peak luminescence over the course of treatment. Accordingly, a curve of magnitude greater than the upper limit of the normal reference range, occurring pre-symptomatically, is useful for informing the individual that he or she may feel unwell and may present symptoms of an infection within a finite period of time, for instance within 1 or 2 days, following the time of providing the blood sample.

Light response curves for samples taken from individuals suffering from a bacterial infection tend to show an extremely heightened response and the curves have a characteristic shape. Thus, the testing procedure makes it possible to distinguish between viral infections and bacterial infections. Such a testing procedure, thus, has the ability to identify individuals suffering from bacterial infection, to whom antibiotics may be prescribed, and those suffering from viral infections, where the prescription of antibiotics is unnecessary.

It is possible to produce a library of signature light emission curves which may be used as standards against which a light emission curve produced using leucocytes obtained from a blood sample taken from an individual under test may be compared. Using such a comparison against such standard signature curves, it is possible not only to determine whether or not the light emission response obtained for an individual under test is normal or abnormal but also, if the light emission response is not normal compared to a control, to identify a possible reason for the abnormality. Individuals who, according to the results obtained by the method described, show an abnormal response may then be selected to undergo more detailed medical testing to identify problems.

According to a preferred mode of the method, the light emission curve produced for an individual under test is compared with one or more standard signature curves and the determination is based on the similarity or dissimilarity occurring between features of the light emission curve and features of the one or more standard signature curves. Preferably, the features of the light emission curve and the features of the one or more standard signature curves are selected from curve shape, intensity of curve and a combination thereof. Typically, the one or more standard signature curves with which the light emission curve produced for an individual under test will be compared will be selected from curves produced using leucocytes obtained from blood samples of individuals clinically confirmed as suffering from infections.

The method is useful for detecting the presence of an infection agent in the body of an individual, such as a bacterial infection agent or a viral infection agent. In particular, the method is useful for detecting the presence of an upper respiratory tract infection agent, such as a rhinovirus or an influenza virus, in the individual.

The shapes of the light emission curves obtained according to the present invention are dependent on the response of the leucocytes, in terms of the production of free radicals and/or other active substances, to activation by an activator. These responses are dependent on the physiological state of the leucocytes in the blood and are thus related to the physiological or medical state of the patients from whom the blood samples were obtained. While such subjective observations of the shapes of the curves are of great value in making diagnoses, a method of quantifying the curves would lead to a more objective determination of irregularities in the leucocytes in the blood and, hence, a more objective diagnosis.

The curves consist of a plot of the response of a luminometer in terms of Relative Light Units (RLU) in three parts. The first part records the light emission before the stimulation of the leucocytes by the activator and may be analysed separately, if at all. The major part of the curve consists of a rise followed by a fall. The whole of this part of the curve can be analysed as one unit or it can be divided into the rising part and the falling part and the two parts analysed separately.

Suitable software can be used to derive a cubic expression of the general form $ax^3+bx^2+cx+d$ that closely fits the major part of a curve. By comparing values of a, b, c and d, calculated from different curves, it is possible to make a quantitative, and therefore more objective, comparison of the responses obtained using blood samples from different patients.

The method can be carried out using conventional apparatus capable of monitoring and/or measuring light emitted by a luminescence reagent in the presence of activated leucocytes. The method is suitable for being carried out in a hand-held luminometer which is highly portable, compact and simple to use. Such a device comprises a means for containing a mixture of the leucocyte sample to be analysed and the luminescence reagent, a means for introducing, into the mixture, an activator, a means for monitoring and/or measuring light emitted by the luminescence reagent over a period of time commencing before and ending after the introduction of the activator, a display for displaying the light emitted by the luminescence reagent and a handle to enable the device to be gripped in one hand.

As described generally above, the compositions of the invention comprise natural products which, in the relative proportions disclosed, appear to stop a respiratory infection, such as a cold, from developing in a subject or, if one is underway, to speed up recovery. In athletes and sports players, one of the effects of intense training and taking part in frequent competitions or games is extreme muscle inflammation, often followed by fatigue. These conditions are frequently accompanied by respiratory and other infections. Muscle inflammation is a normal consequence of training, with damage to muscle fibres leading to the release of inflammatory mediators into the circulation as well as generating reactive oxygen and nitrogen species (RO(N)S). The circulating white blood cells detect these inflammatory mediators (cytokines) and respond by getting ready to leave the circulation and invade the muscles, the site of inflammation. In the muscles, the white blood cells launch an inflammatory response which leads to the release of free radicals and other reactive oxygen species, damaging enzymes and chemical messages to help recruit more white blood cells to the inflammation site. We have found that the administration of compositions of the invention not only help subjects in recovering from respiratory infections of viral origin but also help subjects with depressed respiratory burst activity caused by various states of fatigue, inflammation and other causes of infection. The effects of the compositions of the invention are shown, using the testing procedures described herein, in the following examples.

BRIEF DESCRIPTION OF THE DRAWINGS

FIG. 11A(b) shows a light emission curve obtained using the sample from FIG. 11A(a) one-hour later;

FIG. 11B shows light emission curves obtained using samples from Individual V two and three hours after taking the supplement composition;

EXPERIMENTAL SECTION

Explanations

1. Light Emission Curves

Figure 1A:
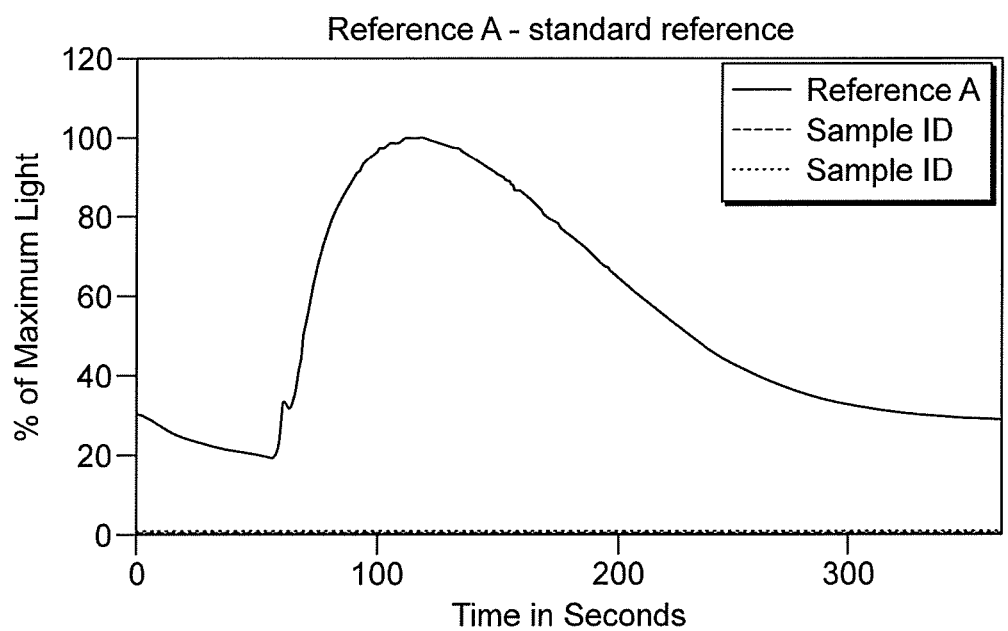
FIGS. 1A(a), 1A(b), 1B(a), 1B(b), 1C(a), and 1C(b) show typical light emission curve shapes, designating as References A to L.
Figure 1A:
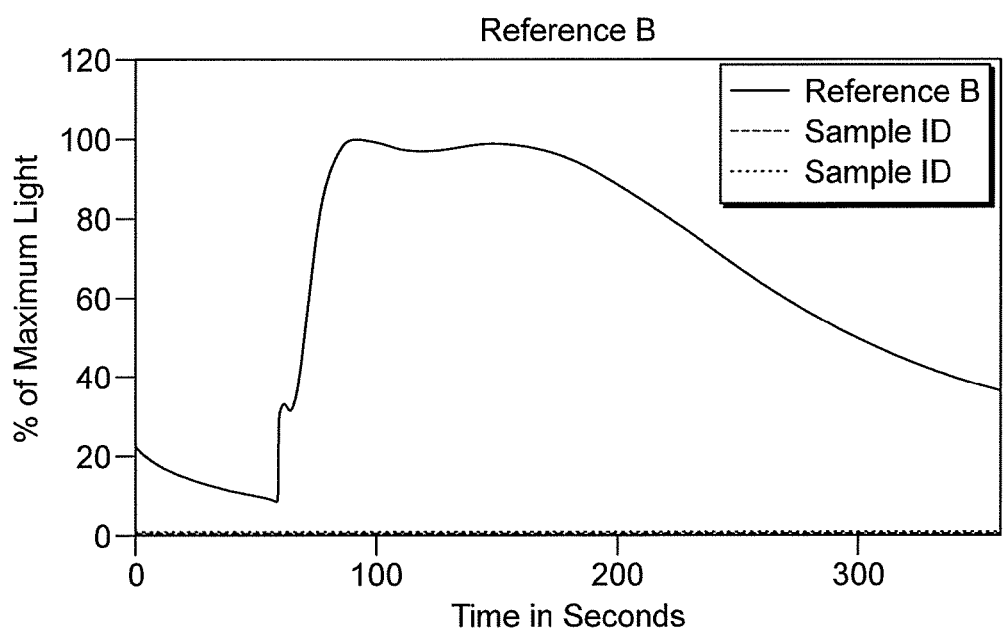
Figure 1A:
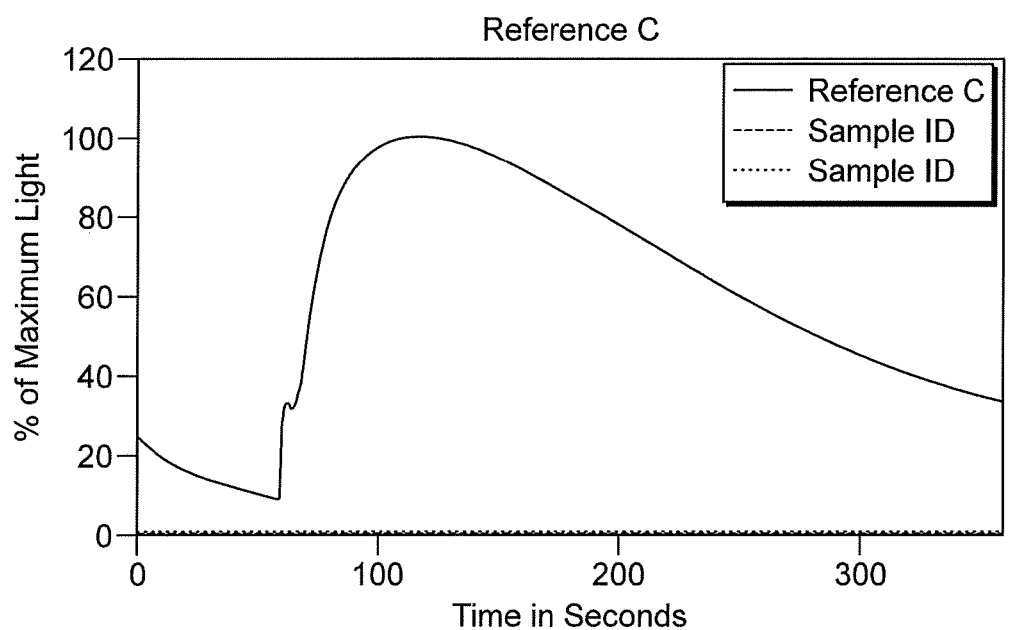
Figure 1A:
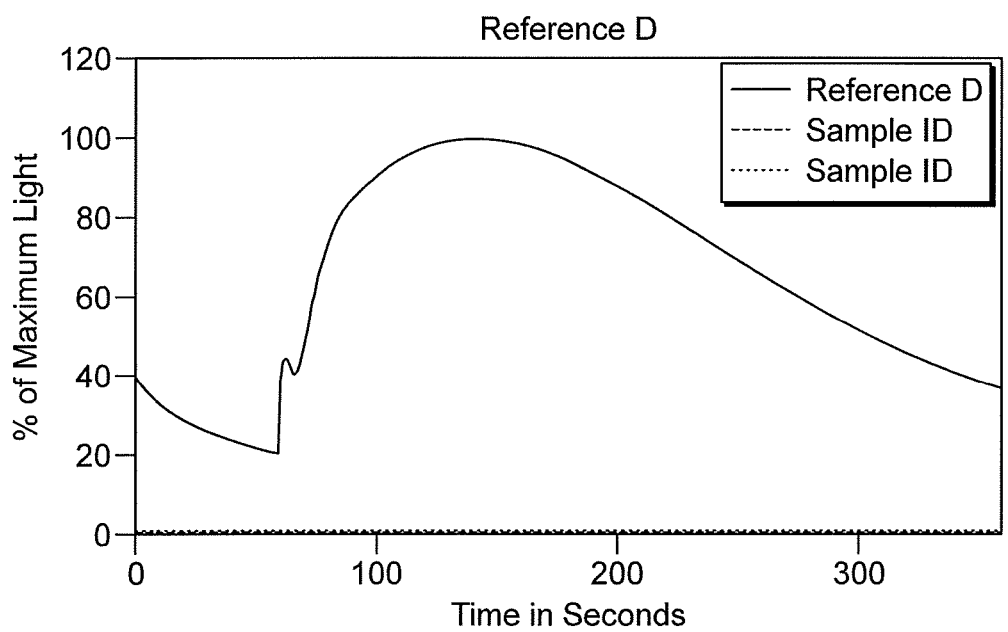
Figure 1B:
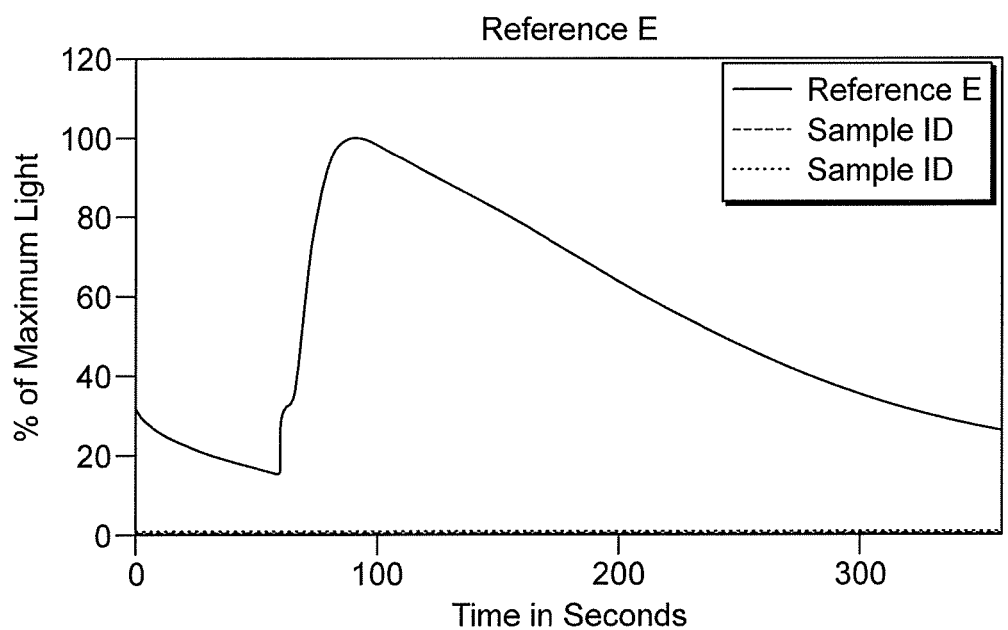
Figure 1B:
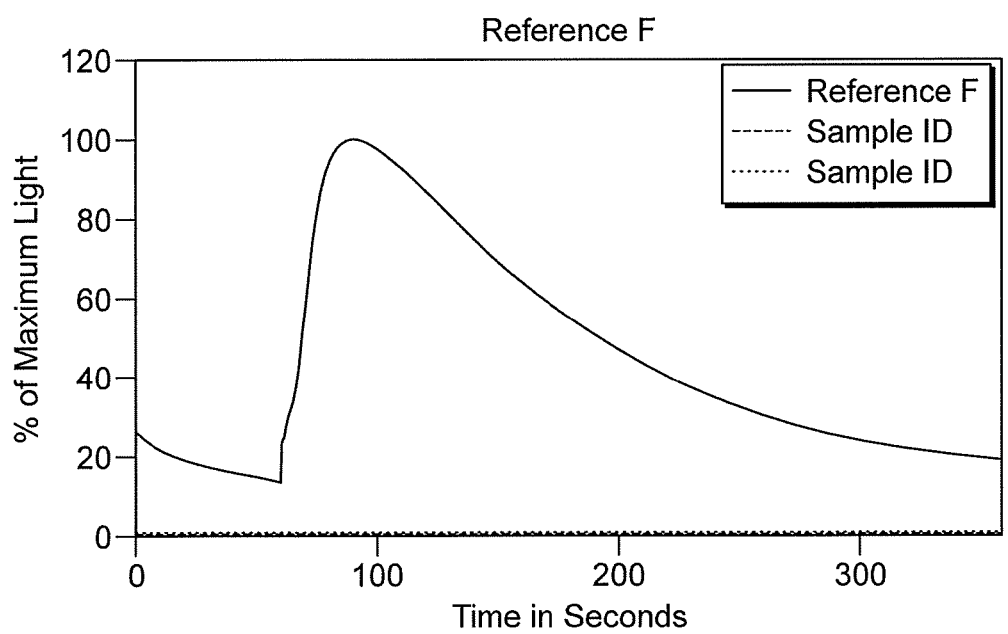
Figure 1B:
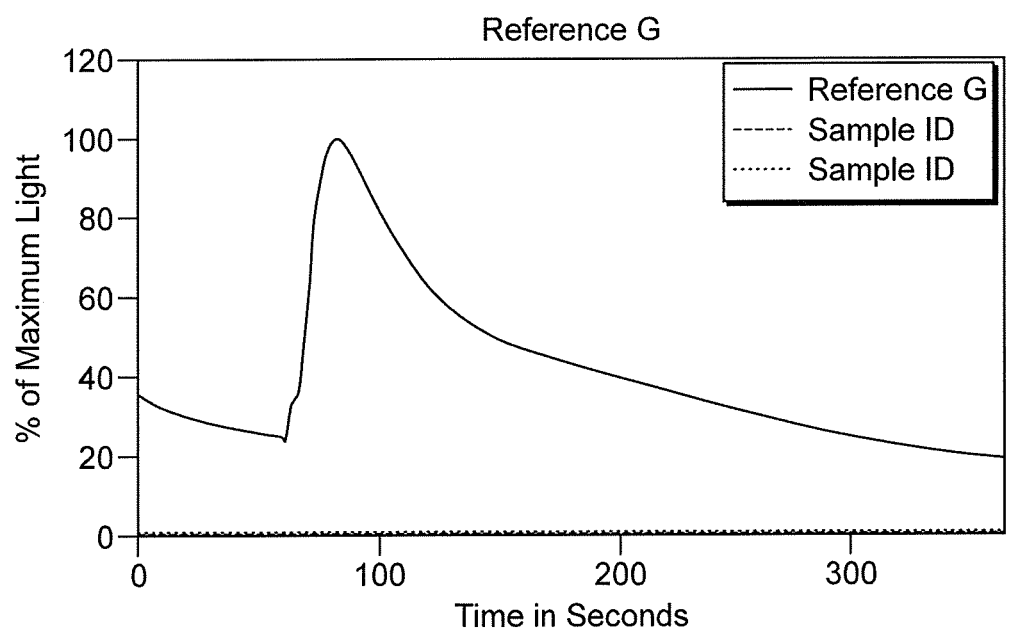
Figure 1B:
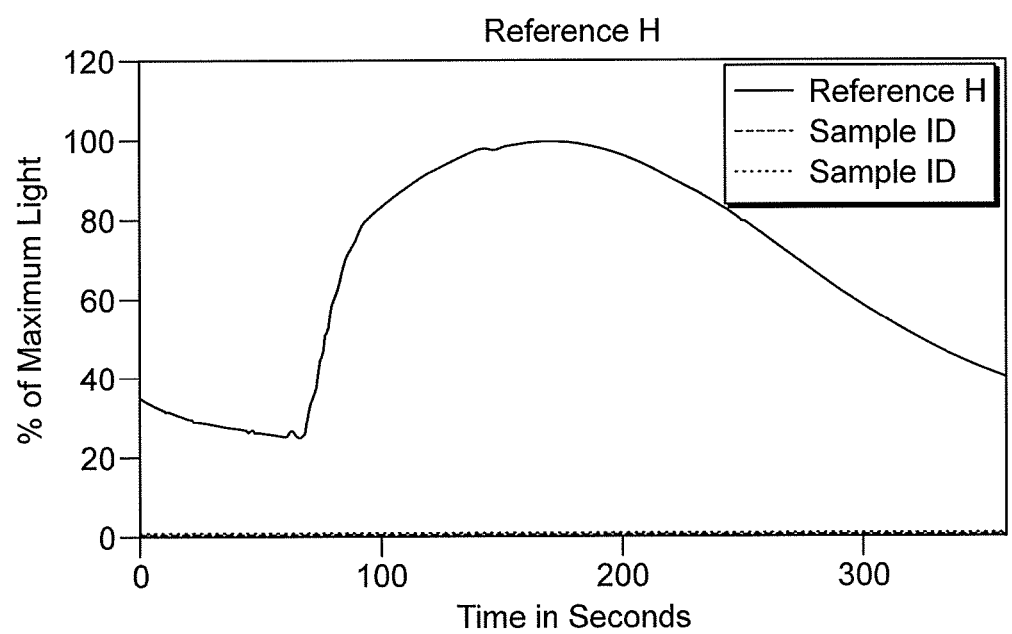
Figure 1C:
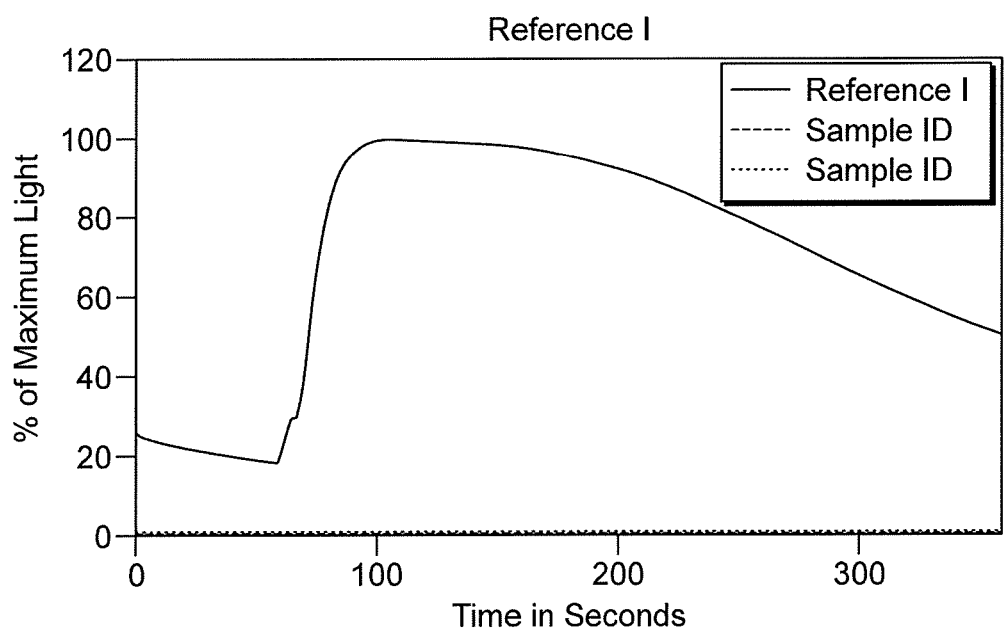
Figure 1C:
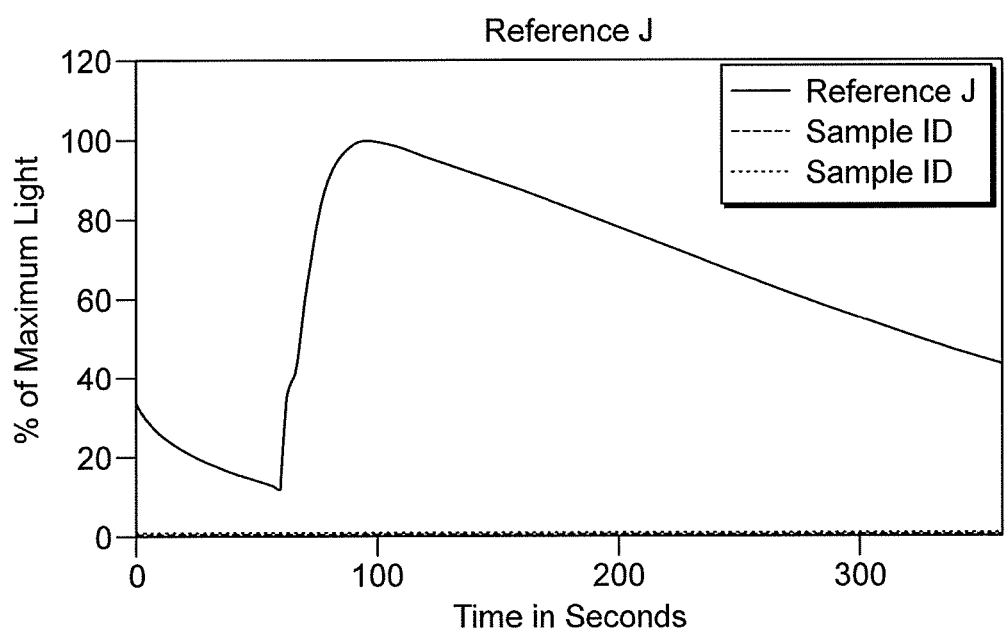
Figure 1C:
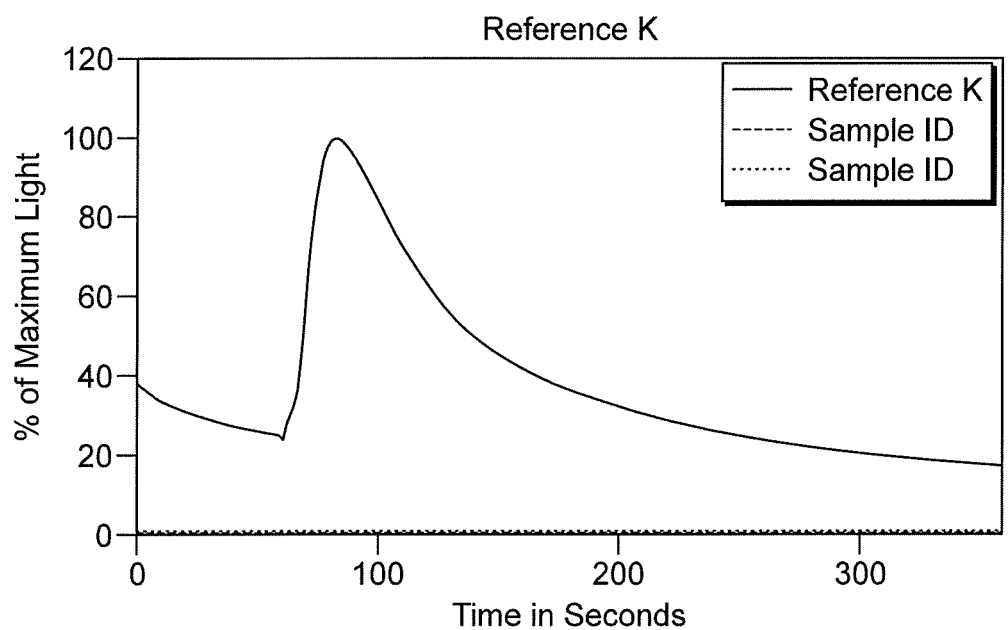
Figure 1C:
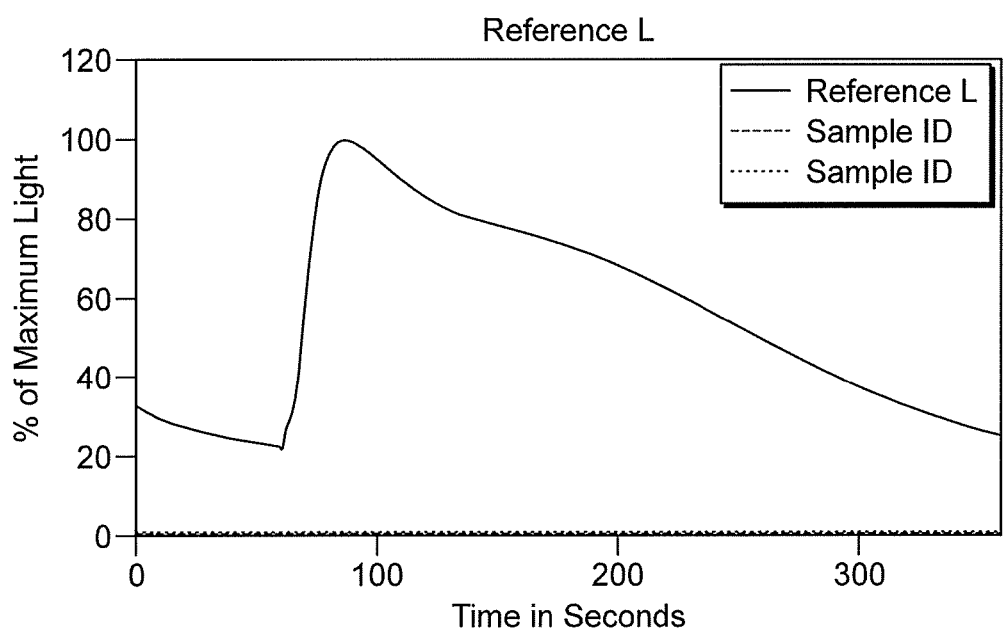

FIGS. 1A, 1B and 1C show a variety of typical light emission curve shapes (shown as Reference A to Reference L). These shapes are derived from actual curves that have been normalized such that the maximum height is always 100%. The final classification of a result obtained experimentally or clinically is derived from both the shape of the curve and the magnitude of the light response. The light emission curve shapes shown in FIGS. 1A to 1C are identified by codes A to L and a brief description of each of these is provided in the table below.

| Shape | Code Comments |
|---|---|
| A | This is the normal reference curve made from the mean of light reference curves produced using blood samples of 385 donors that fall within the normal range. A standard deviation of ±1 is also shown. |
| B | This curve has two peaks, sometimes referred to as double bumps. It is very abnormal and often corresponds to athletes who have been over reaching. Such individuals often end up with upper respiratory tract infections. |
| C | This is close to the normal reference (A) but has two features that set it apart slightly. These are the slight rounded shape and the signal at the end that is above baseline when fMLP was injected. |
| D | This curve is now becoming rounded, a feature we see with a chronic or persistent inflammation, especially when the magnitude is not extremely high. |
| E | Most noticeable is the sharp initial peak and the pronounced steep 'ski' slope. This shape often correlates with stress/intensity of activity and fatigue. |
| F | This shape is like E, but featuring a less steep 'ski' slope. This correlates with stress/intensity of activity and fatigue. |
| G | This shape has two parts to it: the sharp initial peak which, if of great magnitude, would indicate an infection, probably viral, and a distinct change in the shape to 'ski' slope would indicate fatigue. |
| H | Very rounded with the time to peak now shifted to the right at around 200 seconds. If the signal is high then this is probably a bacterial infection. If the signal is very low then this shape would indicate severe fatigue. |
| I | This shape has a hint of B. If it corresponds to a very high signal then it is likely to be a bacterial infection. If the signal is very low then this is one of the very fatigued states. |
| J | This shape is like E with a sharp initial peak and a slightly less step 'ski' slope. This indicates stress/fatigue. |
| K | This shape has a noticeable intense sharp initial peak and very slight change in the slope. If the peak attained is very high then this shape often indicates viral infection and/or inflammation. |
| L | Intense initial peak with a characteristic second peak at around 200 seconds. This strongly suggests over reaching and infection which could be bacterial. |

2. Antioxidant Capacity Scores: $EC_{50}$ Values and ABEL-RAC Mg Scores

Separate light response curves are produced for each concentration of a material tested as well as the no sample control. The results are presented as $EC_{50}$ values and ABEL-RAC scores. The $EC_{50}$ (effective concentration mg) is the concentration (normalised to g/L or mg/mL) of a material that reduces the light (produced with Pholasin® and the free radical or other reactive oxygen species) by 50%. This reduction in light is the antioxidant capacity of the test material.

The greater the amount of material that is required to reduce the light by half, the weaker the antioxidant capacity. The amount of material required to reduce the light by half is termed the $EC_{50}$ (50% effective concentration). Materials with very high antioxidant have very low $EC_{50}$ values. To make it more readily understandable, these $EC_{50}$ values have been converted to positive relative antioxidant capacity scores (ABEL-RAC mg scores) for each free radical or oxidant used to challenge the test material. For example, when peroxynitrite is used as the ROS challenge, the result will be expressed as ABEL-RAC mg peroxynitrite. For superoxide challenge, the result will be expressed as ABEL-RAC mg superoxide. ABEL-RAC mg scores are the reciprocal of the $EC_{50}$ values multiplied by 100 ($1/EC_{50} \times 100$). The higher ABEL-RAC mg score, the higher the antioxidant capacity of the sample.

Figure 4:
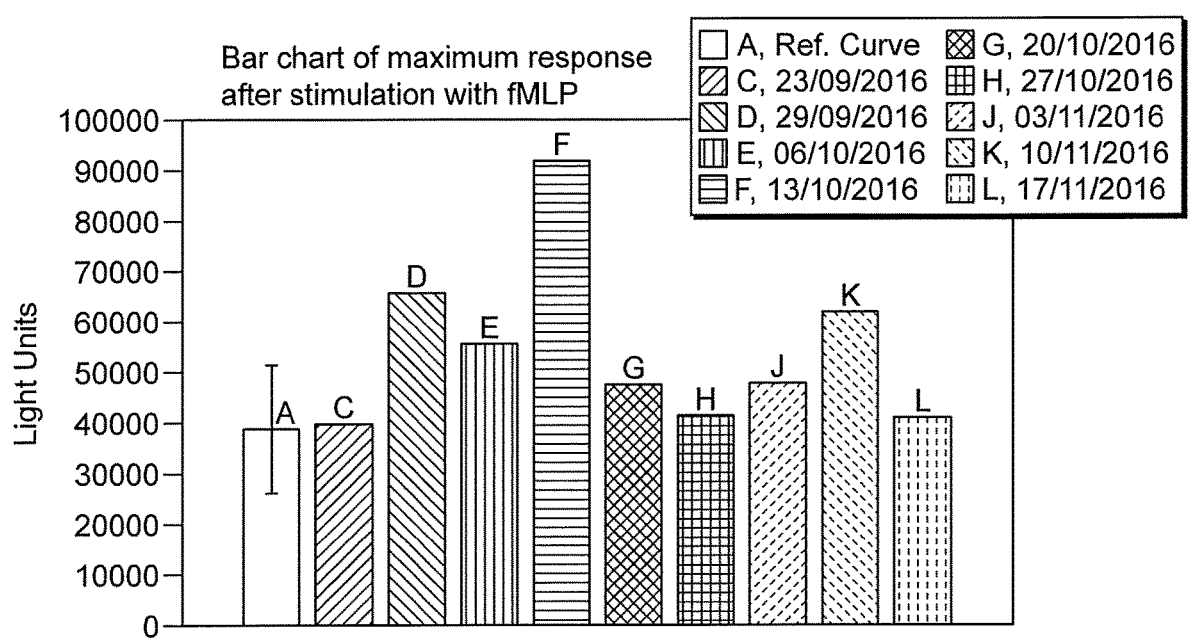
FIG. 4 shows a bar chart illustrating the maximum responses, according to the light emission curves for Individual I.

In FIG. 4, a sample to be tested for antioxidant capacity is challenged with a particular free radical or oxidant in the presence of the light-emitting protein Pholasin®. The concentration that reduced the light by 50% is determined from the results of a range of concentrations and analysed using an exponential regression curve. A template is used to obtain this value. This is the effective concentration ($EC_{50}$) of the sample. The $EC_{50}$ is converted to an ABEL-RAC™ score using the formula: $1/EC_{50}$ (mg)$\times 100$. ABEL-RAC™ scores, for all the different challenges, can be expressed per mg, per dose or percentage in a formula as well as per unit cost.

ABEL-RAC scores are expressed per mg of dried material or μL of a liquid for each of the ROS used to challenge the material. Some materials will be better antioxidants against some free radicals than others.

Six type-specific antioxidant assays are used in the experiments, each using a different kind of free radical or non-radical ROS challenge. These are:

high concentration superoxide assay
halogenated oxidant (=hypochlorous acid) assay
peroxynitrite assay
hydroxyl radical assay
enzyme generated superoxide assay
peroxyl radical assay
singlet oxygen assay The scores per mg for each ingredient can be used directly in formulations to determine the theoretical total ABEL-RAC score for the finished product. The theoretical score is then compared to the actual score of the finished product. By determining the ratio of the actual to the theoretical ABEL-RAC score, it is possible to quantify positive or negative synergy.

The Table Below Gives a Simple Example to Illustrate this

| INGREDIENTS | ABEL-RAC-mg | PERCENT IN PRODUCT | ABEL-RAC contribution |
|---|---|---|---|
| A | 20000 | 25 | 5000 |
| B | 4000 | 50 | 2000 |
| C | 7000 | 20 | 1400 |
|  | SUM |  | 6400 |
| ABEL-RAC | complete synergy | product | 14600 +1.74 |

All the ABEL-RAC mg scores determined for the different ingredients in the new antioxidant dietary supplement were calculated using peroxynitrite as the ROS challenge.

EXAMPLES

Example 1

The following formulation was prepared.

|  | Amount in composition (mg) | % by weight in composition |
| --- | --- | --- |
| Grapeseed extract | 165 | 34 |
| Green tea extract | 125 | 26 |
| Rice flour | 192.5 | 40 |

The individual components and the complete formulation were each subjected to an antioxidant assay to determine antioxidant activity. The assay used was the ABEL-Peroxynitrite Antioxidant Assay (Knight Scientific Limited).

The assay involves the following steps.

1. Any solid material in the sample to be analysed is ground and the ground sample is either dissolved or suspended in water at a concentration of 50 mg/mL.
2. The assay is performed on a microplate luminometer in which a number of samples are placed in individual wells of the microplate, in the presence of Pholasin (luminescent agent), and light is measured from each well (for a duration of 0.2 seconds) a number of times. The time between light measurements is the cycle time and for the peroxynitrite assay the cycle time is standardized at 38 seconds.
3. The assay starts at time zero with the injection into the microplate well of the reagent that generates peroxynitrite. The peroxynitrite anion is produced continually in the assay. Superoxide and nitric acid are released simultaneously from SIN-1 (3-morpholinosydnoninine hydrochloride) where they react together to produce the peroxynitrite anion ($ONCO^-$) to challenge the sample material.
4. Separate light response curves are produced for each sample tested as well as a no-sample control.
5. Separate assays are carried out using different concentrations of sample. By running a range of concentrations, the concentration of material able to reduce the emitted light by half, the effective concentration ($EC_{50}$) of the sample is determined.
6. From the determined $EC_{50}$ value, a relative antioxidant capacity (RAC) may be calculated. The RAC score is the reciprocal of the $EC_{50}$ value multiplied by 100.

Each of the grapeseed extract, green tea extract, rice flour and the whole formulation was assayed, separately, as described above. The ABEL-RAC scores obtained from the peroxynitrite (POX) assay are shown below. Using the individual POX RAC scores of the ingredients of the formulation, the predicted contribution to the formulation based on individual scores was determined, as shown in the table. This predicted score was compared with the actual score obtained for the whole formulation. The synergy (actual score divided by predicted score) was calculated.

ABEL-RAC Scores in ABEL Peroxynitrite Assay

|  | Amount in final product (mg) | % in final product | POX RAC score | Predicted contribution |
| --- | --- | --- | --- | --- |
| Grapeseed extract | 165 | 34 | 369511 | 126361 |
| Green tea extract | 125 | 26 | 462601 | 119845 |
| Pine Bark extract | 0 | 0 | 347760 | 0 |
| Pomegranate extract | 0 | 0 | 450245 | 0 |
| Rice flour | 192.5 | 40 | 21 | 8 |
| Total weight | 482.5 |  | Predicted score | 246214 |
|  |  |  | KSL mixture scores (actual scores) | 372388 |
|  |  |  | Synergy (Actual ÷ Predicted) | 1.51 |

As shown above, the antioxidant activity of the actual formulation was found to be greater than the predicted activity based on the sum of the activities of the individual ingredients of the formulation. The synergy was calculated as 1.51.

Example 2

A different formulation from that in Example 1 contained 165 mg grapeseed extract, 125 mg of green tea extract and 192.5 mg of rice flour. This formulation and the individual ingredients were assayed, as described in Example 1. The results are shown in the table below.

ABEL-RAC Scores in ABEL Peroxynitrite Assay

|  | Amount in final product (mg) | % in final product | POX RAC score | Predicted contribution |
| --- | --- | --- | --- | --- |
| Grapeseed extract | 165 | 34 | 369511 | 126361 |
| Green tea extract | 142.5 | 30 | 462601 | 136623 |
| Pine Bark extract |  | 0 | 347760 | 0 |
| Pomegranate extract |  | 0 | 450245 | 0 |
| Rice flour | 175 | 36 | 21 | 8 |
| Total weight | 482.5 |  | Predicted score | 262982 |
|  |  |  | KSL mixture scores (actual scores) | 172907 |
|  |  |  | Synergy (Actual ÷ Predicted) | 0.66 |

As shown above, the antioxidant activity of the actual formulation was found to be greater than the predicted activity based on the sum of the activities of the individual ingredients of the formulation. The synergy was calculated as 0.66, lower than the synergy found for the formulation of Example 1.

Example 3

A formulation containing 150 mg grapeseed extract, 132 mg green tea extract, 50 mg of pine bark extract and 50 mg of pomegranate extract was prepared. This formulation and the individual ingredients were assayed, as described in Example 1. The results are shown in the table below.

ABEL-RAC Scores in ABEL Peroxynitrite Assay

|  | Amount in final product (mg) | % in final product | POX RAC score | Predicted contribution |
|---|---|---|---|---|
| Grapeseed extract | 150 | 39 | 381053 | 149628 |
| Green tea extract | 132 | 35 | 347675 | 120139 |
| Pine Bark extract | 50 | 13 | 500148 | 65464 |
| Pomegranate extract | 50 | 13 | 107055 | 14012 |
| Total weight | 382 |  | Predicted score | 349244 |
|  |  |  | KSL mixture scores (actual scores) | 464207 |
|  |  |  | Synergy (Actual ÷ Predicted) | 1.33 |

As shown above, the antioxidant activity of the actual formulation was found to be greater than the predicted activity based on the sum of the activities of the individual ingredients of the formulation. The synergy was calculated as 1.33.

Example 4

An Individual I provided a fresh blood sample for testing, at weekly intervals, starting 23 Sep. 2016. On 23 Sep. 2016, Individual I reported feeling well. On 29 Sep. 2016, the individual reported feeling unwell with a respiratory infection. On 13 Oct. 2016, Individual I was given a dose of the formulation described above in Example 3.

The blood samples were tested according to the method described herein on the same day the samples were taken.

Each blood sample was collected in a tube containing EDTA. 2 ml of Blood Dilution Buffer were added to an empty tube and, to this, were added 20 µl of the EDTA blood to prepare a diluted whole blood sample for testing. The tube was capped and then gently inverted three times to mix the contents of the tube.

To a polystyrene transparent cuvette was added 222 µL RECONSTITUTION AND ASSAY BUFFER FOR PHO-LASIN® (Knight Scientific Limited), 50 µL reconstituted ADJUVANT-K ("ADJUVANT-K" is a trade mark of Knight Scientific Limited) which is a luminescence enhancer, 125 µL PHOLASIN® and 50 µL diluted whole blood. The reconstituted ADJUVANT-K luminescence enhancer had previously been prepared from ADJUVANT-K reconstituted with 5 mL RECONSTITUTION AND ASSAY BUFFER. The cuvette was capped and contents mixed by inverting the tube 3 times. The cuvette with all the reagents and blood put into an incubator at 37° C. for 6 minutes. (As the incubation time must be a minimum of 5 minutes but exceeding 6 minutes is acceptable, it is possible to incubate more than one sample at the same time).

After 6 minutes, the cap was removed from the cuvette and attached to a black tube extender and inserted into the ABELmeter, an ultrasensitive tube luminometer. 50 µl of fMLP was then loaded into an injection and inserted into the ABELmeter.

Figure 16:
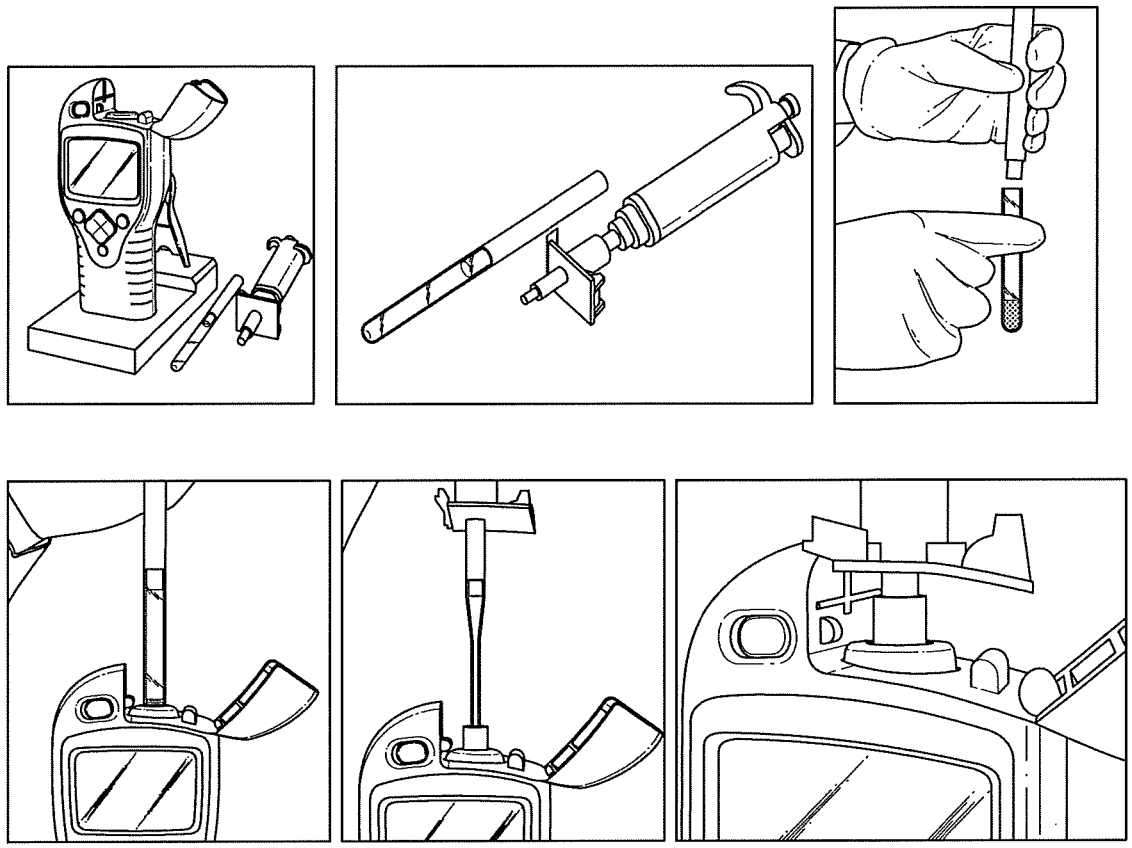
FIG. 16 shows the ABELmeter top left (unassembled), middle top the injection pipette and the black tube extender with a cuvette attached, top right the tube extender being fitted to the cuvette, containing all the reagents, bottom left the cuvette being loaded in the ABELmeter, bottom middle the injection cuvette, pre-loaded with fMLP, being loaded into the ABELmeter, and bottom right showing everything mounted ready to start an assay.

FIG. 16 shows the ABELmeter top left (unassembled); middle top the injection pipette and the black tube extender with a cuvette attached; top right the tube extender being fitted to the cuvette, containing all the reagents; bottom left the cuvette being loaded in the ABELmeter; bottom middle the injection cuvette, pre-loaded with fMLP, being loaded into the ABELmeter and bottom right, showing everything mounted ready to start the assay.

The assay was started and light emitted from the sample in the cuvette was recorded continually for 1 minute at intervals of 0.5 seconds. After 1 minute, the 50 µl of fMLP was dispensed into the cuvette with light emitted recorded continuously for a further 5 minutes.

The light emission profile was recorded as a light emission curve showing the light emitted for the period commencing 1 minute before the addition of the fMLP activator and ending 5 minutes after the addition of the activator, fMLP.

Figure 2:
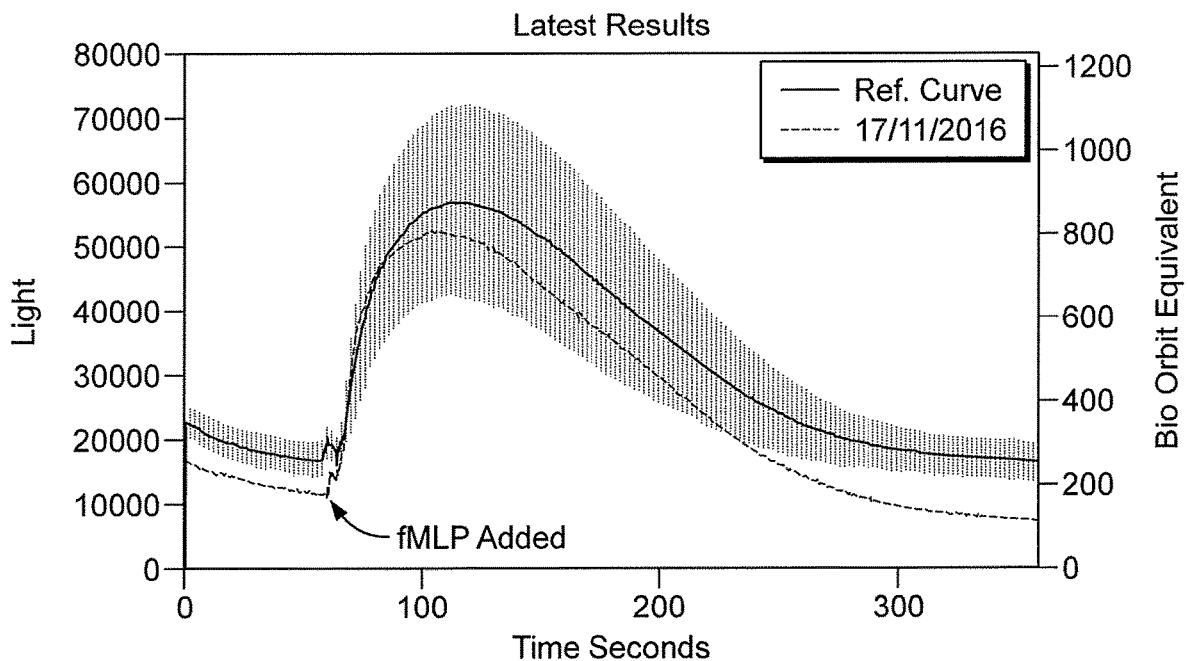
FIG. 2 shows a light emission curve obtained for a sample from Individual I and a standard reference curve relating to a normal, healthy human.

The light emission curve obtained for the sample taken on 17 Nov. 2016 is shown in FIG. 2, where curve A is the light emission curve obtained using the sample taken from Individual I and curve B is a standard reference curve relating to a normal, healthy human. The shaded area denotes the tolerance around the standard reference curve B.

Figure 3:
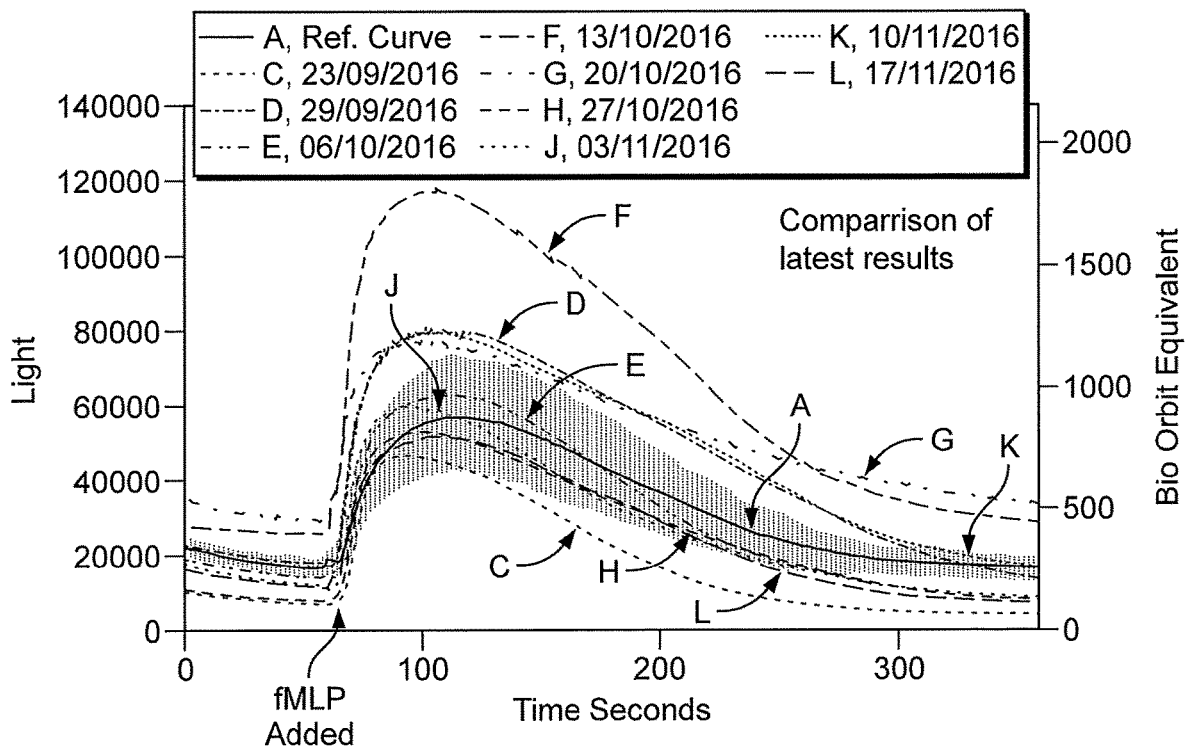
FIG. 3 shows, superimposed, all light emission curves produced using blood samples taken from Individual I over a test period.

FIG. 3 shows, superimposed, all light emission curves produced using blood samples taken from Individual I over the test period. The curves are referenced as follows: C dated 23 Sep. 2016, D dated 29 Sep. 2016, E dated Jun. 10, 2016, F dated 13 Oct. 2016, G dated 20 Oct. 2016, H dated 27 Oct. 2016, J dated 3 Nov. 2016, K dated 10 Nov. 2016 and L dated 17 Nov. 2016. In these curves, it will be seen that curve F shows an excessive response following the addition of the activator to the leucocyte/luminescence reagent mixture. It shows an extremely steep increase in light emission following the addition of the fMLP activator, which is steeper than that of the reference curve (ref). The peak light emission reached in curve F is much greater than that in the reference curve. Subsequent to the administration of the composition of the invention (on 13 Oct. 2016) the peak light emissions of curves produced for subsequent blood samples taken decreases and the light emission curves have a shape that approaches the shape of the reference curve.

A bar chart showing the maximum responses, according to the light emission curves, is shown in FIG. 4. The heightened responses of D and E indicate the existence of the infection in Individual I as it progressed up to 13/10/2106 before a dose of the composition was administered.

Example 5

An initial sample of blood was provided by an individual II and this sample was tested according to the procedure described above in Example 4. This initial blood sample gave an elevated signal compared to a standard reference relating to a normal, healthy human. The signals obtained using further blood samples throughout the day were monitored. Two hours after the initial sample was tested, the composition described in Example 1 was administered to the individual in capsule form. Periodically, further blood samples were taken from the individual and these were tested according to the procedure described in Example 4.

Figure 5:
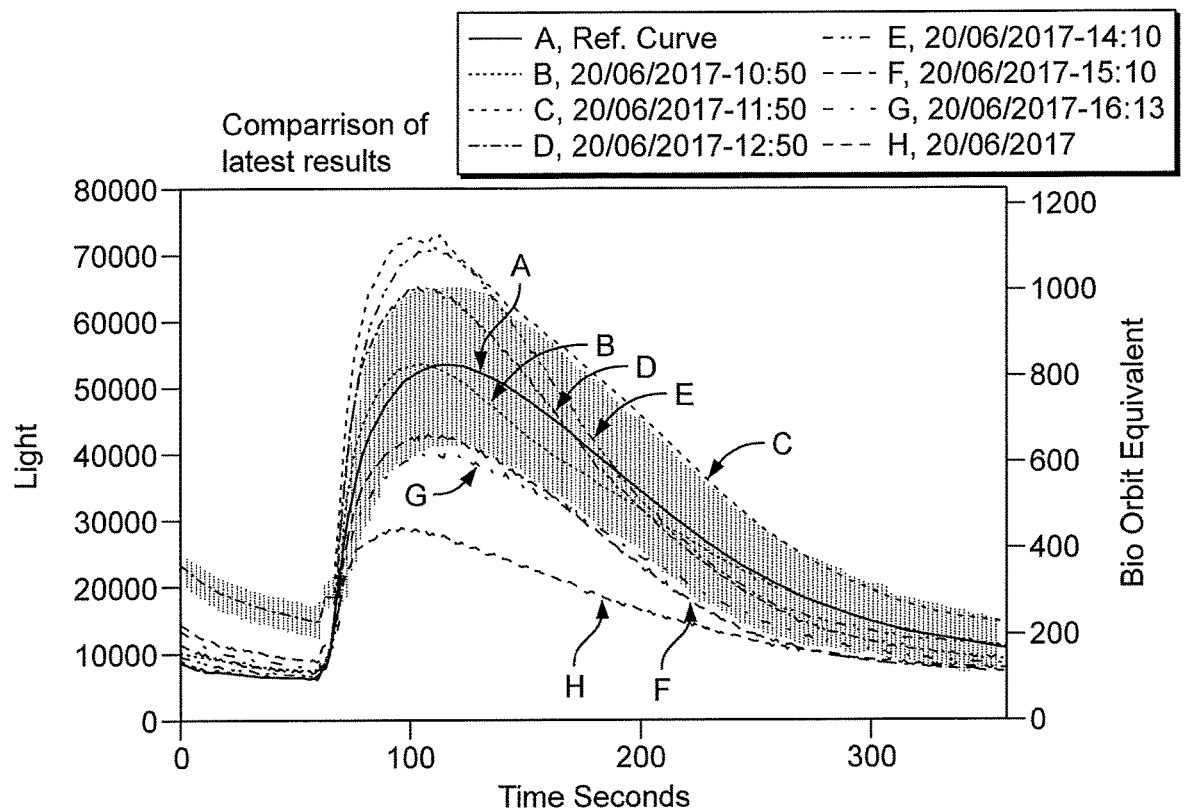
FIG. 5 shows, superimposed, all light emission curves produced using blood samples taken from individual II over a test period.

FIG. 5 shows, superimposed, all light emission curves produced using blood samples taken from individual II over the test period. The curves shown in FIG. 5 are referenced as follows: curve A is the reference curve relating to a normal, healthy human; B is the light emission curve produced using the initial blood sample provided at the start of the monitoring period (time 10.50; 20/06/2017); C is the light emission curve produced using a blood sample provided one hour later (11.50; 20/06/2017); D is the curve produced using a further blood sample provided 2 hours after the initial sample (12.50; 20/06/2017); E is the curve produced using a further blood sample provided 80 minutes after the individual took the administered formulation (14.10; 20/06/2017); F is the curve produced using a blood sample provided 140 minutes after the individual took the administered formulation (15.10; 20/06/2017); G is the curve produced using a blood sample provided 203 minutes after the individual took the administered formulation (16.13; 20/06/2017); H is the curve produced using a blood sample provided after a further 60 minutes (17.13; 20/06/2017). A bar chart showing the maximum responses, according to the light emission curves, is shown in FIG. 6.

Figure 6:
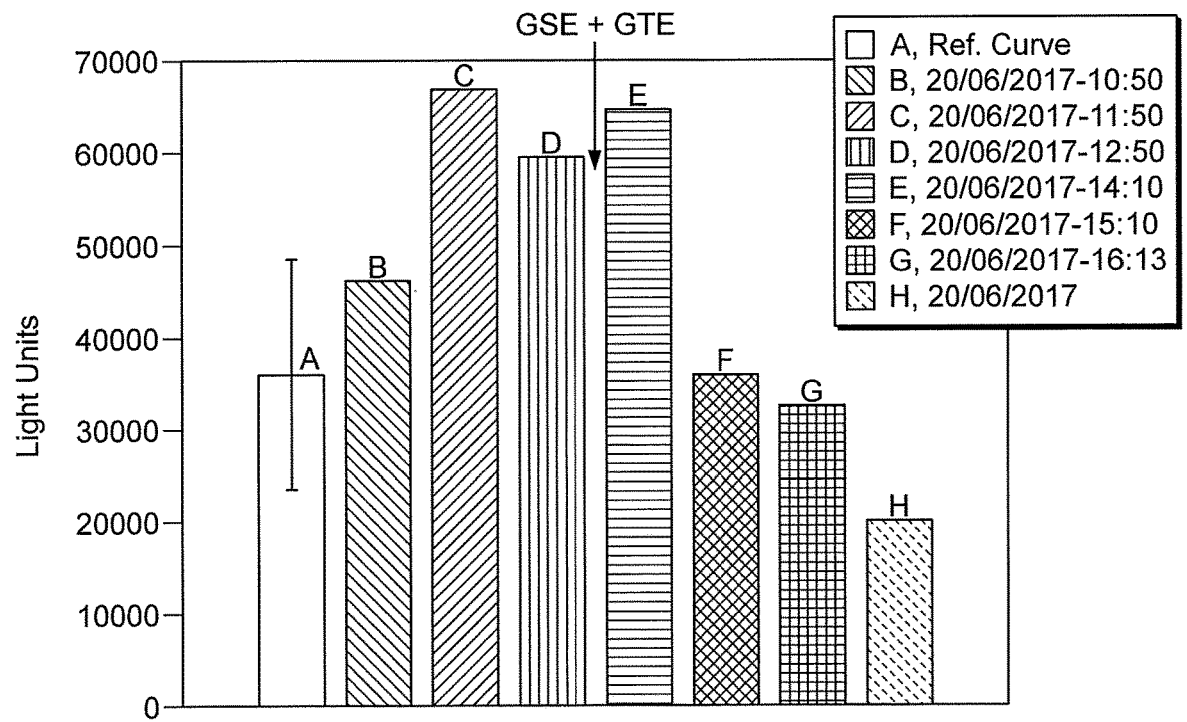
FIG. 6 shows a bar chart illustrating the maximum responses, according to the light emission curves for Individual II.

As shown in FIGS. 5 and 6, the administration of the formulation, although an initial increase in response was observed (curve E), resulted in a subsequent rapid decrease in signal (curves F, G, H) leading to a depressed white blood cell response. One explanation of the depressed white blood cell response as indicated by these later signals is that the antioxidant activity of the formulation has been absorbed by the cells. The later curves F to H showed a gradual improvement of the curve shape approaching the shape of the reference curve A.

Example 6

An Individual III provided a fresh blood sample for testing, at intervals of a few days, starting on 23 Sep. 2016. On 23 Sep. 2016, the individual reported feeling well. On 29 Sep. 2016 the individual reported feeling unwell with a cold. A dose of the composition according to Example 3 was given to the individual on that day. The blood samples taken were tested in accordance with the test procedure described above in Example 4. Since symptoms were in evidence again, according to the results for the sample taken on 13 Oct. 2016, a further dose of the composition was taken by the individual on that day.

Figure 7:
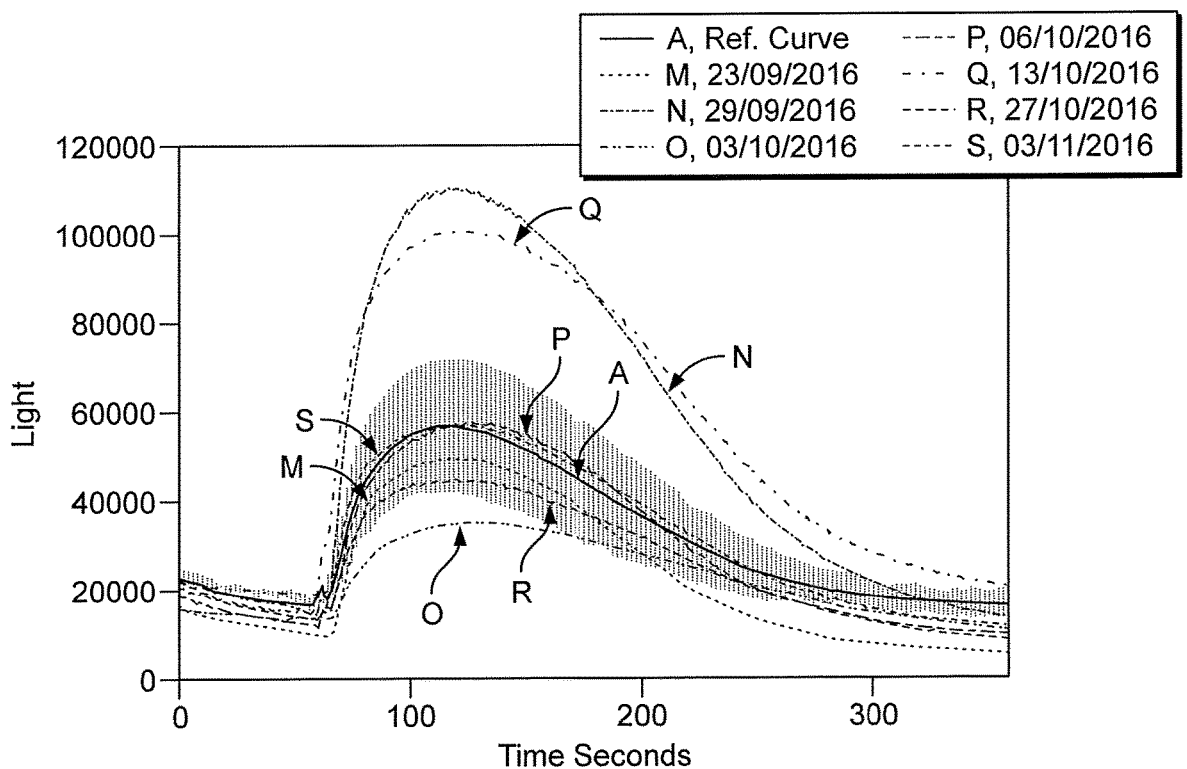
FIG. 7 shows, superimposed, all light emission curves produced using blood samples taken from individual III over a test period.

FIG. 7 shows, superimposed, all light emission curves produced using the blood samples taken from the individual. These curves are referenced as follows: M dated 23/9/16, N dated 29/9/16, 0 dated Mar. 10, 2016, P dated Jun. 10, 2016, Q dated 13/10/16, R dated 27/10/16 and S dated Mar. 11, 2016.

Curve N shows a heightened response following the addition of the fMLP activator to the leucocyte/luminescence reagent mixture compared to the reference curve (ref) and an extremely steep increase in light emission. Thus response, shown in curve N, is indicative of the presence of infection. Following administration of the composition of the invention on 29/9/16 the light response curves for the next two blood samples taken were subdued. However, the infection was then seen to progress again (see curve Q) and a further dose of the composition was administered on 13/10/16. The light response curves S and T for the final blood samples taken can be seen to be returning to normality compared to the reference curve.

Figure 8:
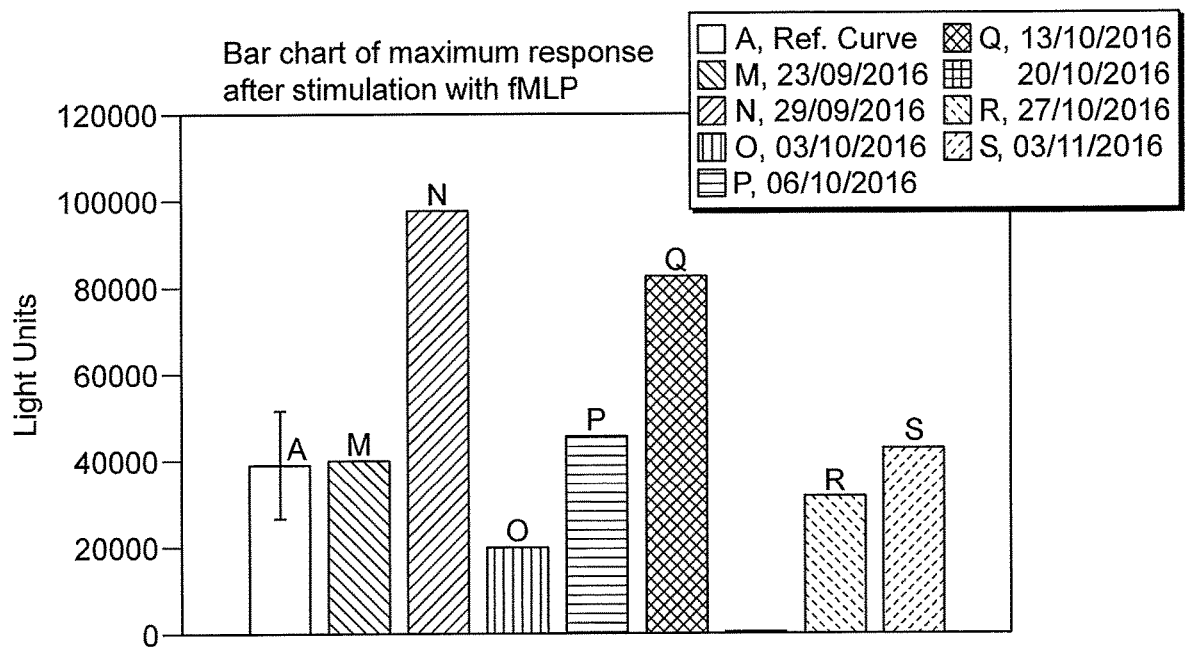
FIG. 8 shows a bar chart illustrating the maximum responses, according to the light emission curves for Individual III.

FIG. 8 is a bar chart showing the maximum light emission responses according to the curves M to T. The heightened responses of N and Q indicate the extent of infection at those times in the individual tested.

Example 7

An individual IV provided a fresh blood sample for testing, at intervals of a few days, starting on 23 Sep. 2016. On that day, the individual reported having cold/influenza-type symptoms and was given a dose of the composition according to Example 3 on that day. The blood samples taken were tested in accordance with the procedure described in Example 4. The results obtained for the sample taken on 23 Sep. 2016 showed a slight elevation in light response compared to the reference. A blood sample taken for testing on 3 Oct. 2016, i.e. 10 days after the individual was administered the composition of the invention, gave a light response that was decreased compared to that of 23 Sep. 2016 although, on that day, the individual reported that he was still feeling ill. A blood sample taken on 6 Oct. 2016 was tested and this gave a very high light response signal. The light response curve obtained for this sample had a very high peak and a rounded shape, characteristic of a bacterial infection. Antibiotics were administered to the individual on that day to combat the bacterial infection. After 7 days, the individual reported feeling better. A blood sample taken on 13 Oct. 2016 was tested and was found to give a much decreased light response approaching that of the reference.

Figure 9:
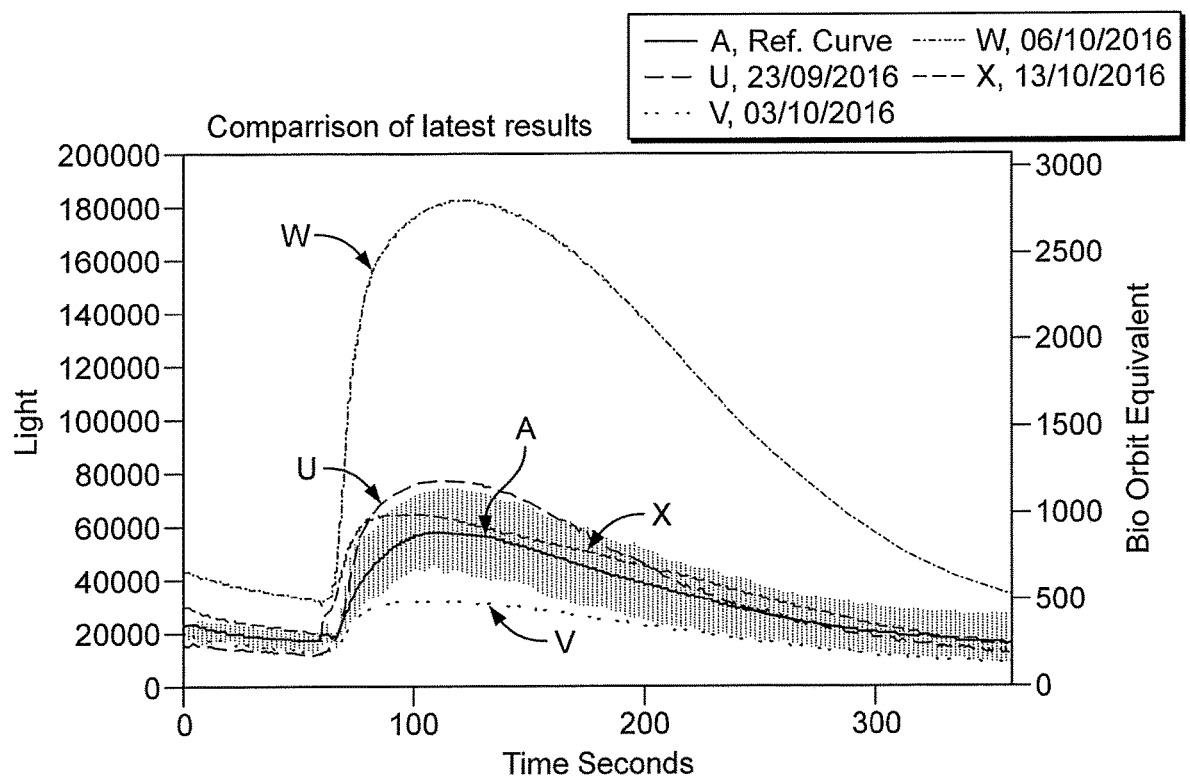
FIG. 9 shows, superimposed, all light emission curves produced using blood samples taken from individual IV over a test period.
Figure 10:
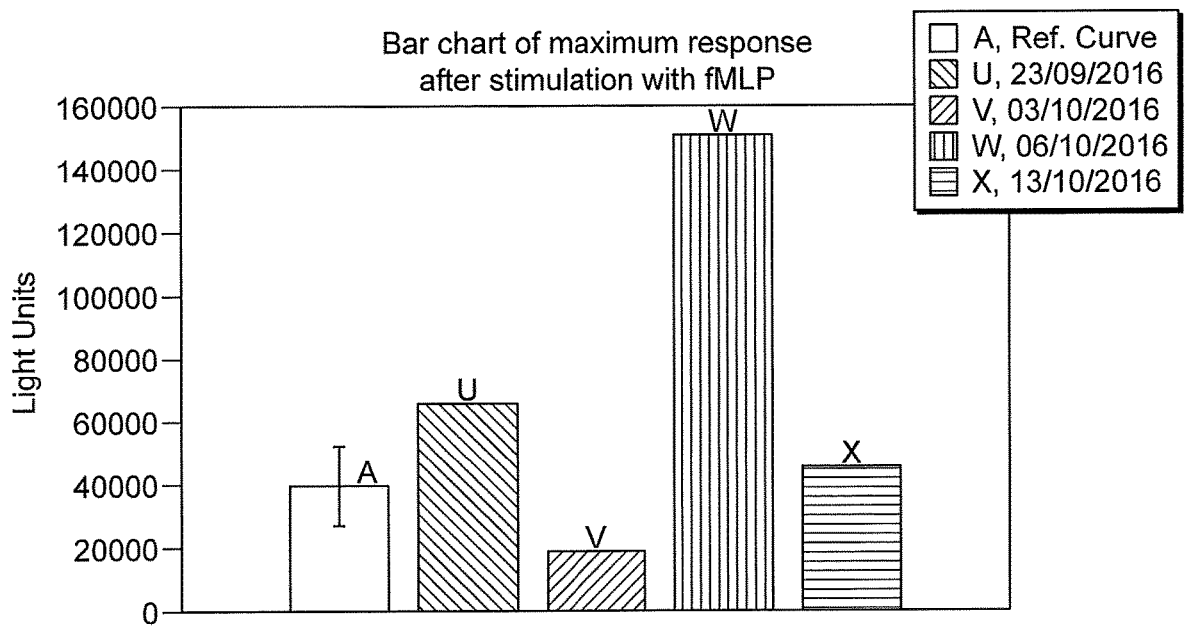
FIG. 10 shows a bar chart illustrating the maximum responses, according to the light emission curves for Individual IV.

FIG. 9 shows, superimposed, all light emission curves produced using the blood samples taken from Individual IV. These curves are referenced as follows: U dated 23 Sep. 2016, V dated 3 Oct. 2016, W dated 6 Oct. 2016 and X dated 13 Oct. 2016. Curve U shows a response heightened compared to the reference curve (ref). Curve V shows a subdued response compared to both curve U and the ref. Curve W, produced three days after curve V, shows a very heightened response. The very high peak and rounded shape of this curve is indicative of the presence of a bacterial infection. After the bacterial infection had been treated, the blood sample taken one week later gave, on testing, curve X which shows a response that is slightly higher than normal, compared to the reference curve, but which is approaching normal levels. The maximum light emission responses, according to the curves U to X, are shown in the bar chart (FIG. 10).

The example shows that the testing procedure can distinguish between a viral infection and a bacterial infection on the basis of the light response obtained from a blood sample. This testing procedure makes it possible to defer the administration of antibiotics to an ill person until a light response indicative of a bacterial infection is obtained thus avoiding the administration of antibiotics to persons showing only the signs of a viral infection.

Example 8

Figure 11A:
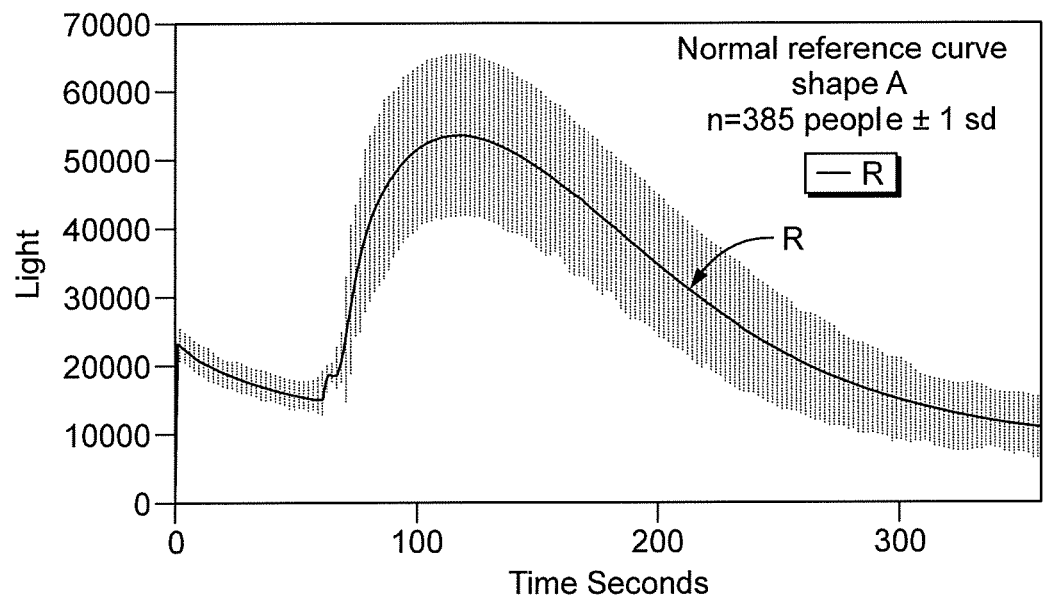
FIG. 11A(a) shows a light emission curve obtained for a sample from Individual V.
Figure 11A:
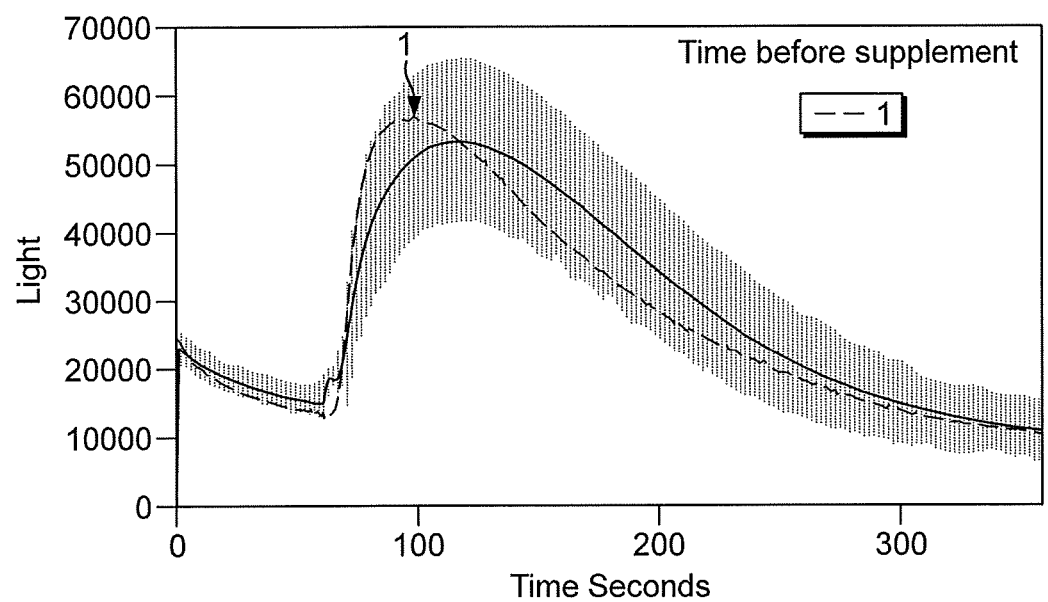
Figure 11A:
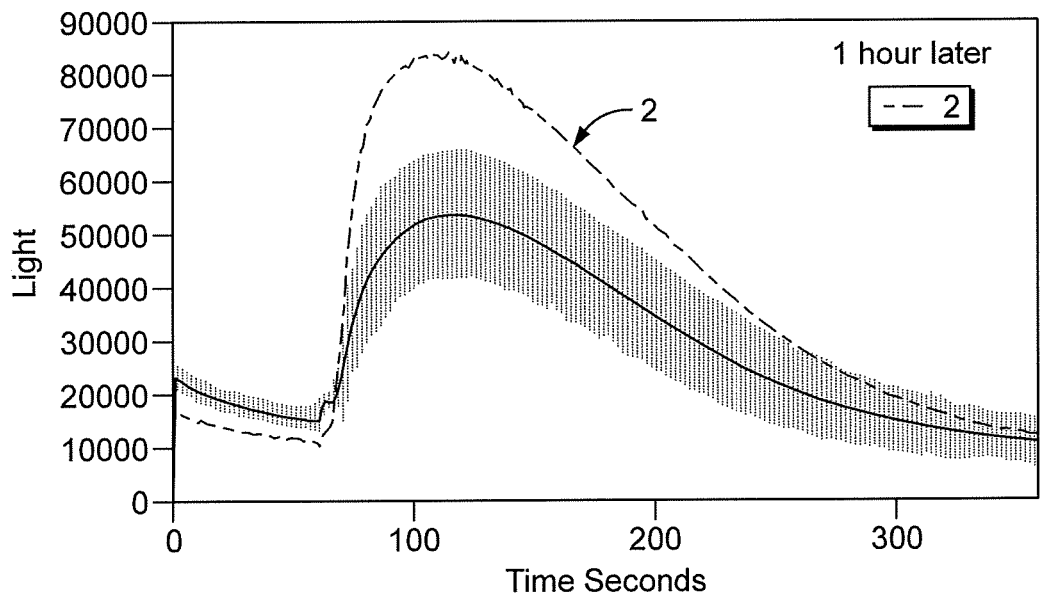
Figure 11B:
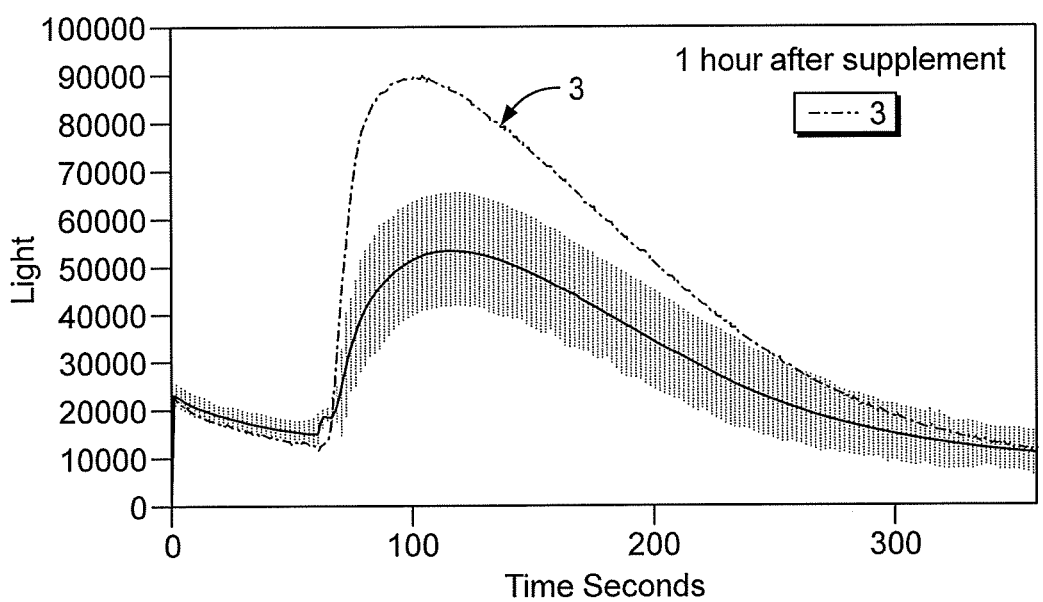
FIG. 11B(a) shows a light emission curve obtained using a sample from Individual V one hour after taking a supplement composition.
Figure 11B:
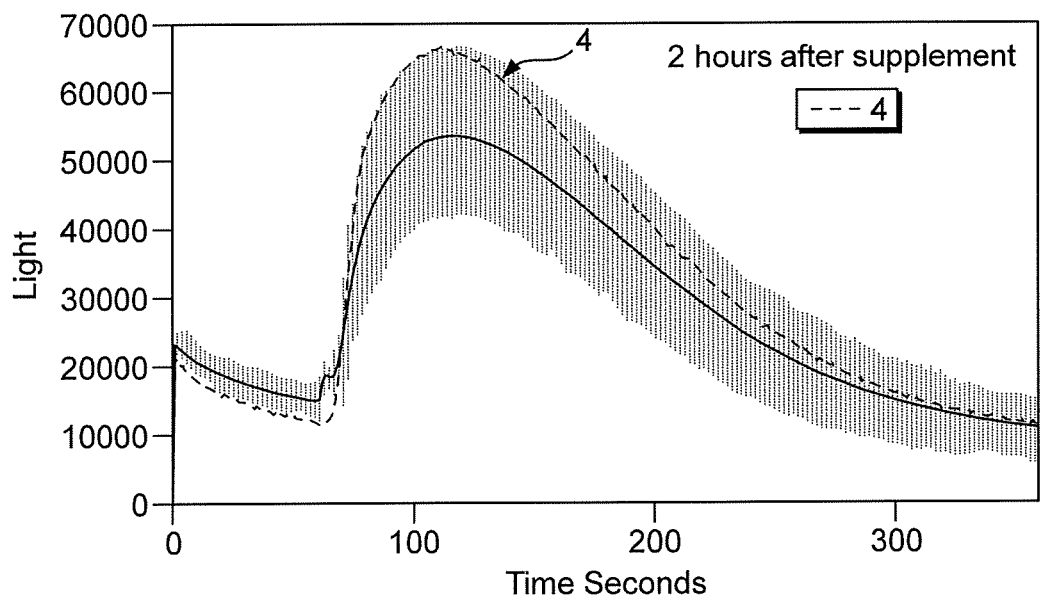
Figure 11B:
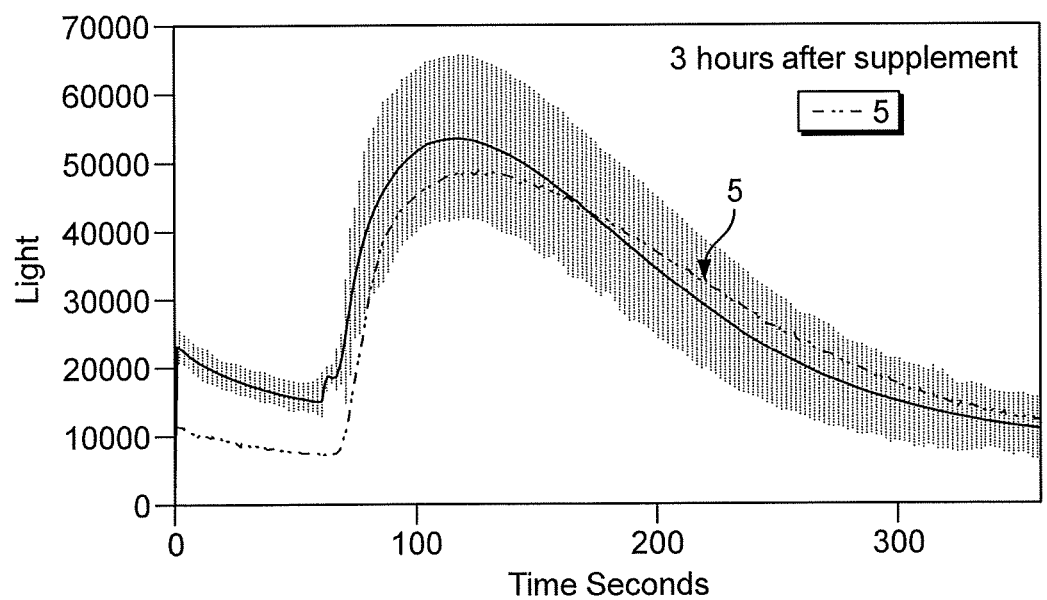

A male individual V claimed to be feeling a little unwell and stressed. A sample of blood was provided by the individual at that time and this was subjected to testing according to the procedure described in Example 4 above. The light emission curve obtained using this blood sample is shown in the bottom graph of FIG. 11A(*a*). FIG. 11A(*a*) also shows, as a reference, the normal reference curve shape A (top graph). As can be seen from FIG. 11A(*a*), the shape of the light emission curve obtained for the blood sample tested is similar to reference curve shapes F and G (FIG. 1B), suggesting the possibility of an onset of an infection. One hour later, another sample of blood was provided by the individual and this was then subjected to testing according to the above-described procedure. The light emission curve obtained using this one-hour later sample is shown in FIG. 11A(*b*). As can be seen, the response was above the upper limit of the normal range. The individual then took one capsule of the 4-ingredient supplement composition described in Example 3 above. After a further one-hour period, another blood sample was provided by the individual and was subjected to testing according to the above-described procedure. The light emission curve for this blood sample is shown in FIG. 11B(a) which shows a response even higher than that shown in FIG. 11A(b). Another blood sample was taken one hour after that tested in FIG. 11B(a) (i.e. two hours after taking the supplement composition) and this was subjected to testing according to the described procedure. The light emission curve obtained is shown in the top graph of FIG. 11B(b) from which it can be seen that the response signal had decreased from that shown previously in FIG. 11B(a). After another one hour delay (i.e. 3 hours after the individual had taken the supplement composition) a further blood sample was taken and tested. The shape of the light emission curve obtained (bottom graph of FIG. 11B(b)) shows that the response had decreased further (compared to the top graph of FIG. 11B(b)) and was in the normal range (cf. normal reference curve shape A). The shape of the curve was rounder than previously with a clear shift of the peak to the right compared to the shapes of the curves shown in FIGS. 11A(a) (bottom graph) and 11A(b) produced prior to the time when the individual had taken the supplement composition.

Figure 11C:
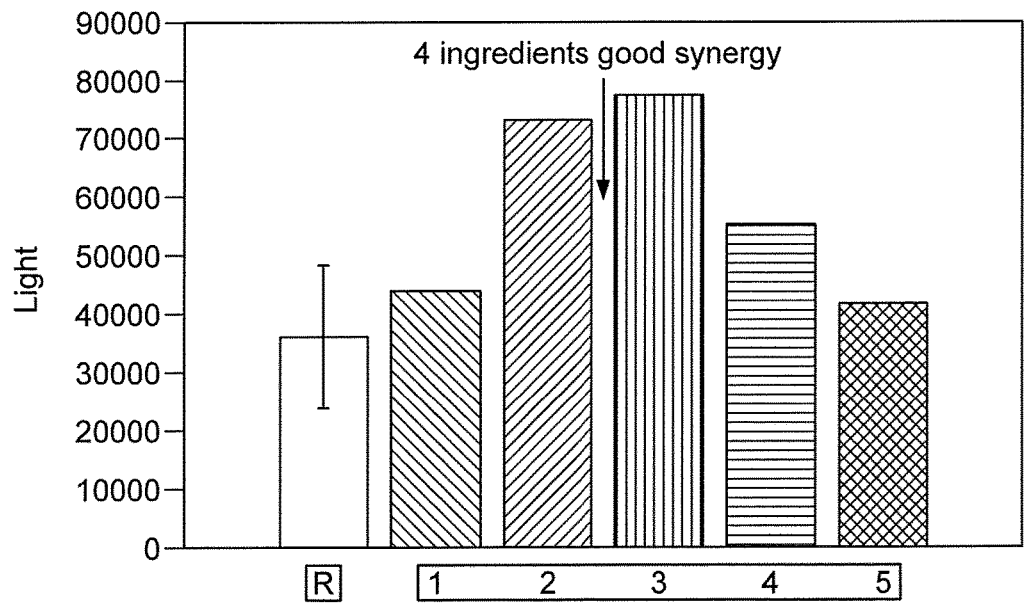
FIG. 11C shows a bar chart illustrating the maximum responses, according to the light emission curves for Individual V.

FIG. 11C is a bar chart which shows the maximum light emission responses according to the normal reference and to the curves shown in FIGS. 11A(a) and (b) and FIGS. 11B(a) and (b). The point at which the supplement composition was taken by the individual under test is also indicated.

Example 9

Figure 12A:
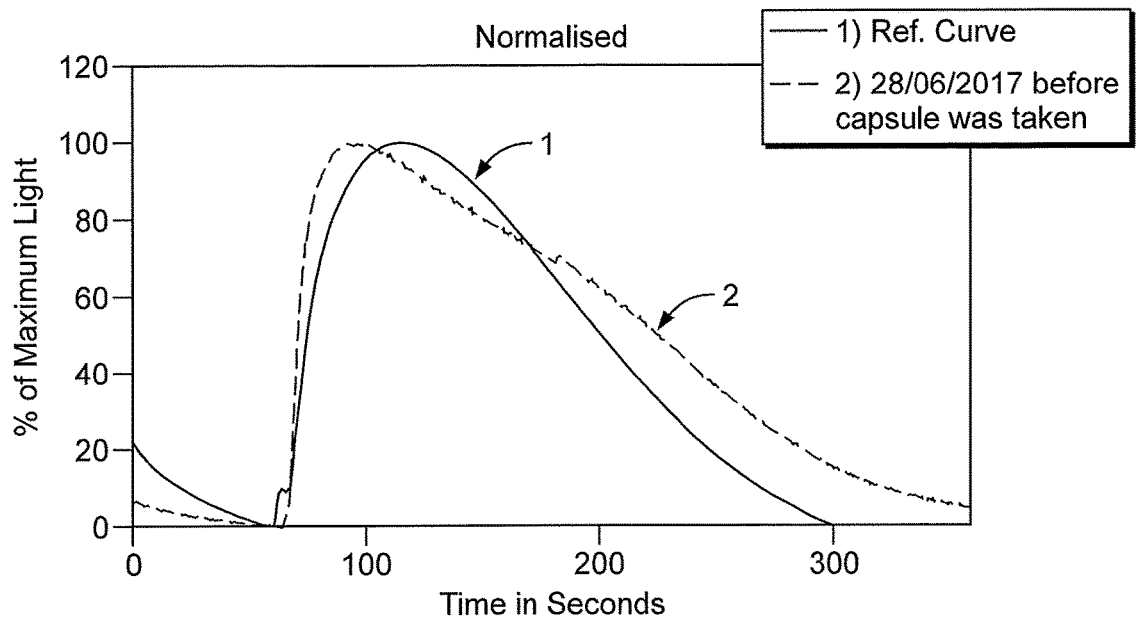
FIG. 12A shows a light emission curve obtained for a sample from Individual VI.
Figure 12B:
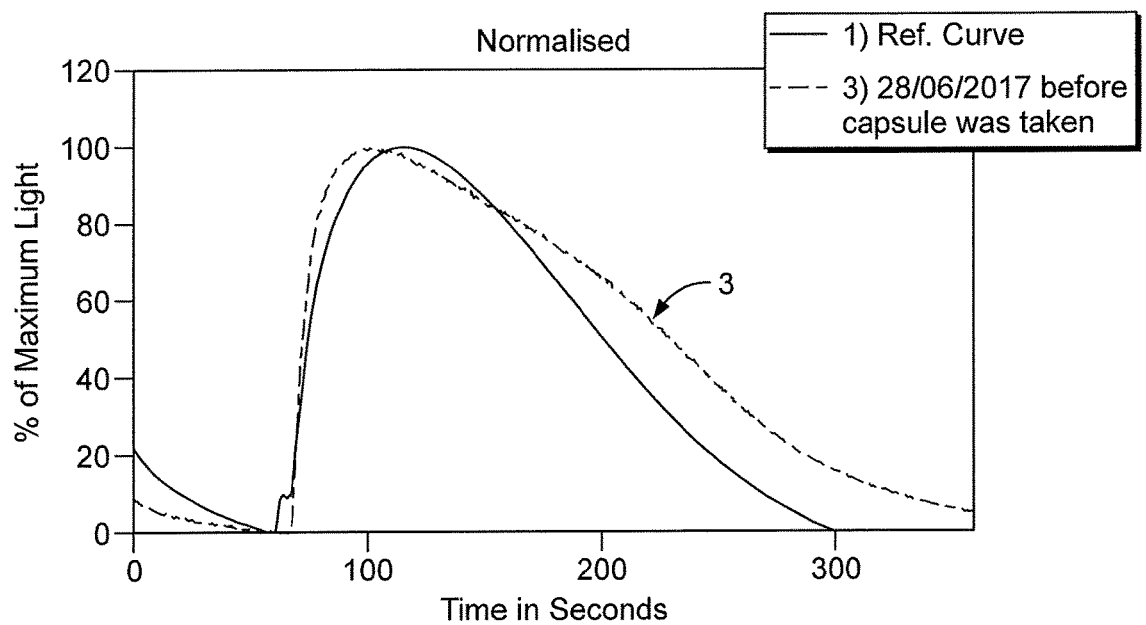
FIG. 12B shows shows a light emission curve obtained for a sample from Individual VI, taken one hour after the sample for FIG. 12A.
Figure 12C:
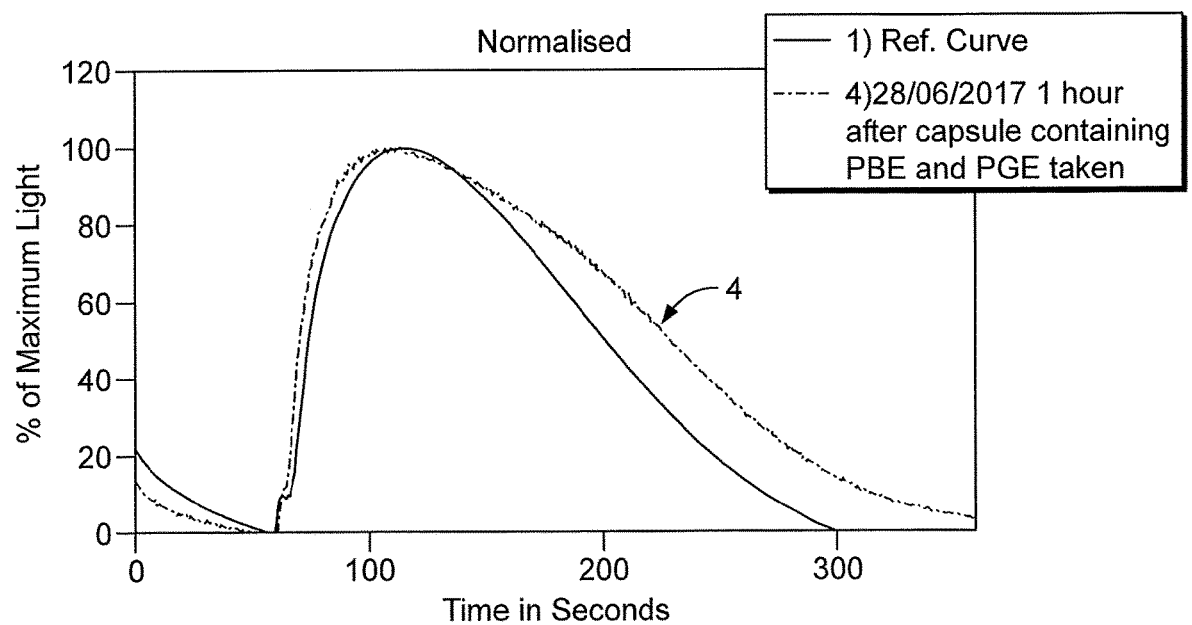
FIG. 12C shows a light emission curve obtained for a sample from Individual VI taken 1 hour after administration of a two-component supplement formulation.
Figure 12D:
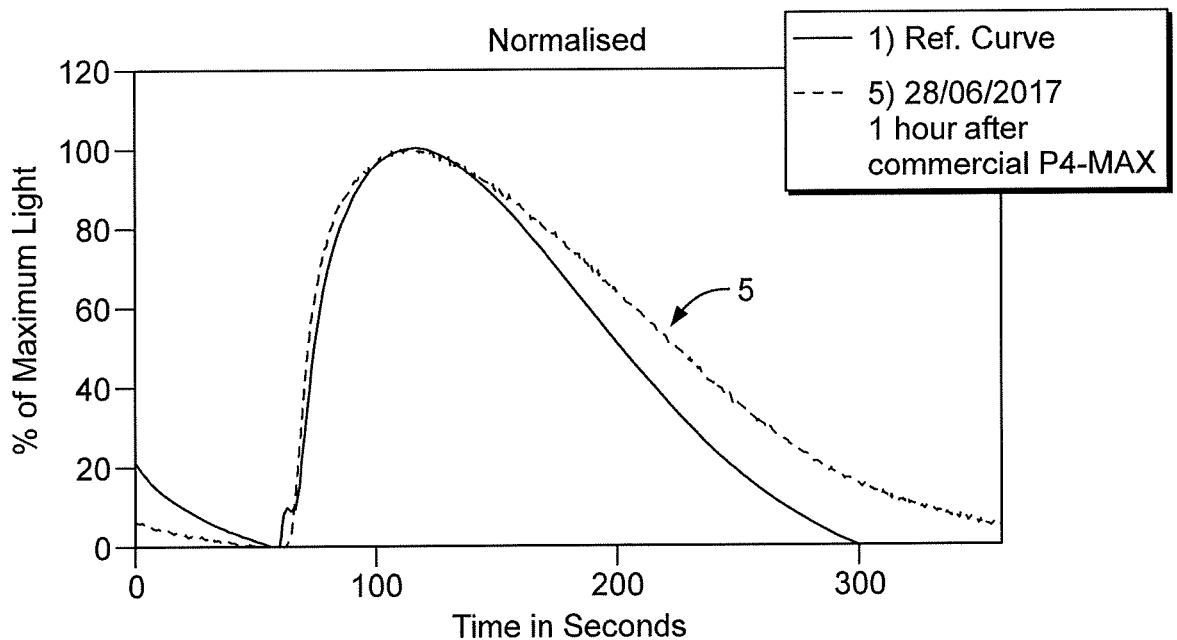
FIG. 12D shows a light emission curve obtained for a sample from Individual VI taken 1 hour after administration of a 4-component formulation as described in Example 3.
Figure 12E:
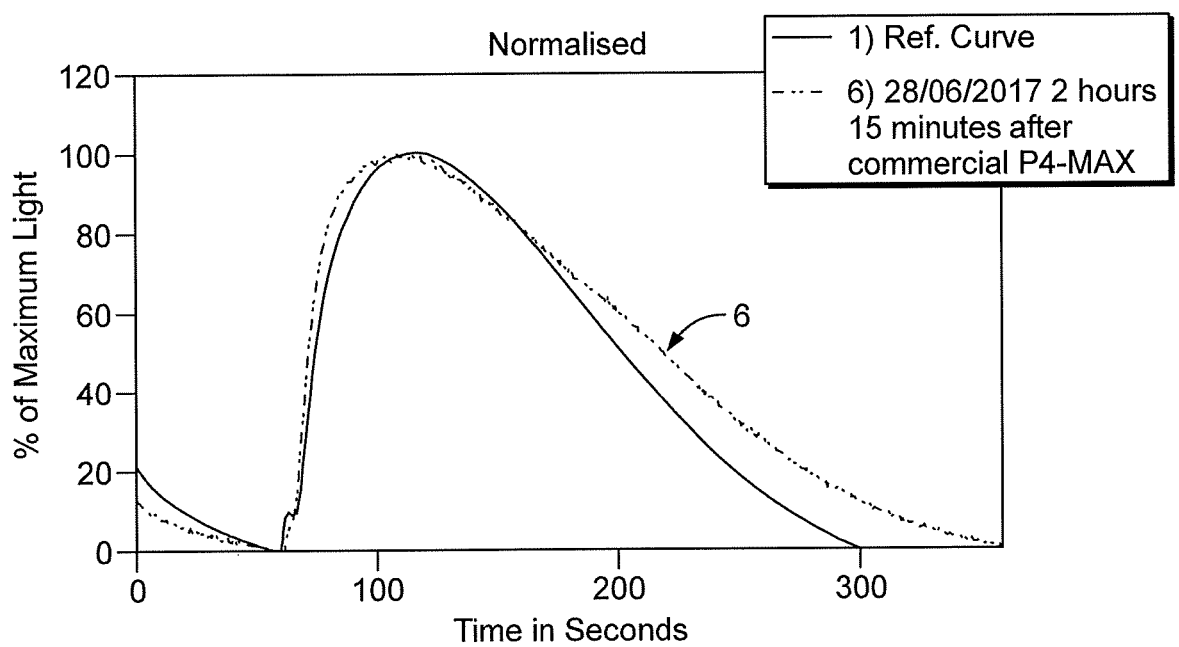
FIG. 12E shows light emission curve obtained for a sample from Individual VI taken 2 hours 15 minutes after the administration of the 4-component formulation referenced in FIG. 12D.

A blood sample provided by an individual VI gave a light emission curve (FIG. 12A; 2) showing an abnormal response compared to a reference curve relating to a normal, healthy human (FIG. 12A; 1). A second sample was provided 1 hour after the first and the curve produced (FIG. 12B; 3) still had an abnormal shape. A formulation containing 50 mg pine bark extract and 100 mg pomegranate extract was then administered in a capsule to the individual. A blood sample was taken from the individual 1 hour after administration of the two component formulation. The curve (FIG. 12C; 4) produced for this blood sample showed a reduction in cell response but no noticeable change to the shape. A 4-component formulation as described in Example 3 was administered to the individual in capsule form and one hour after this administration a further blood sample was provided. The curve produced for this blood sample (FIG. 12D; 5) had a shape approaching that of the reference curve. The curve produced using a blood sample provided 2 hours 15 minutes after the administration of the 4-component formulation confirmed the gradual changing of the curve shape closer to that of the reference curve (FIG. 12E; 6) and that the signal had reduced to be within the normal range.

Example 10

Figure 13A:
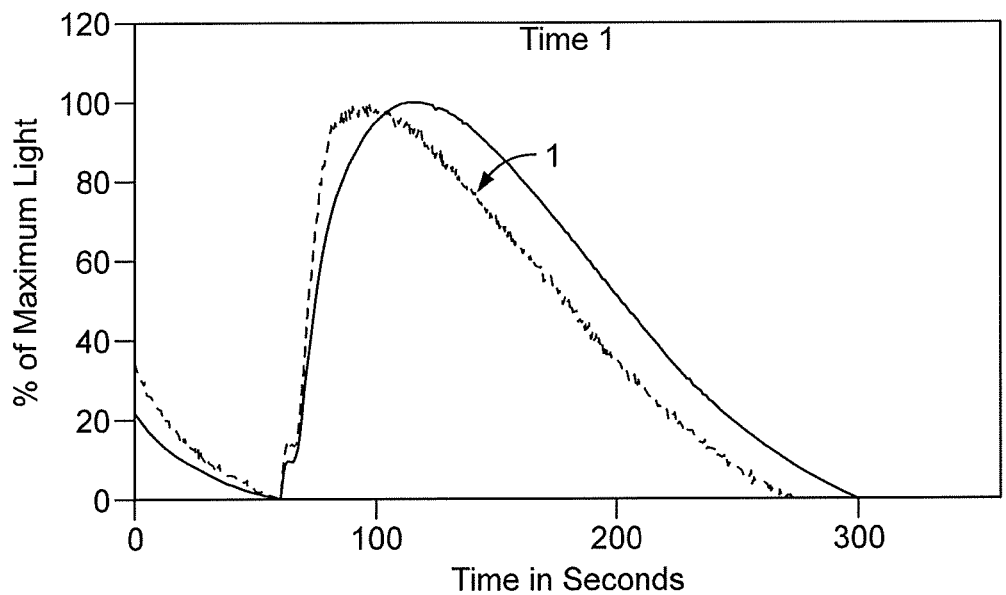
FIG. 13A shows a light emission curve obtained for a sample from Individual VII.
Figure 13B:
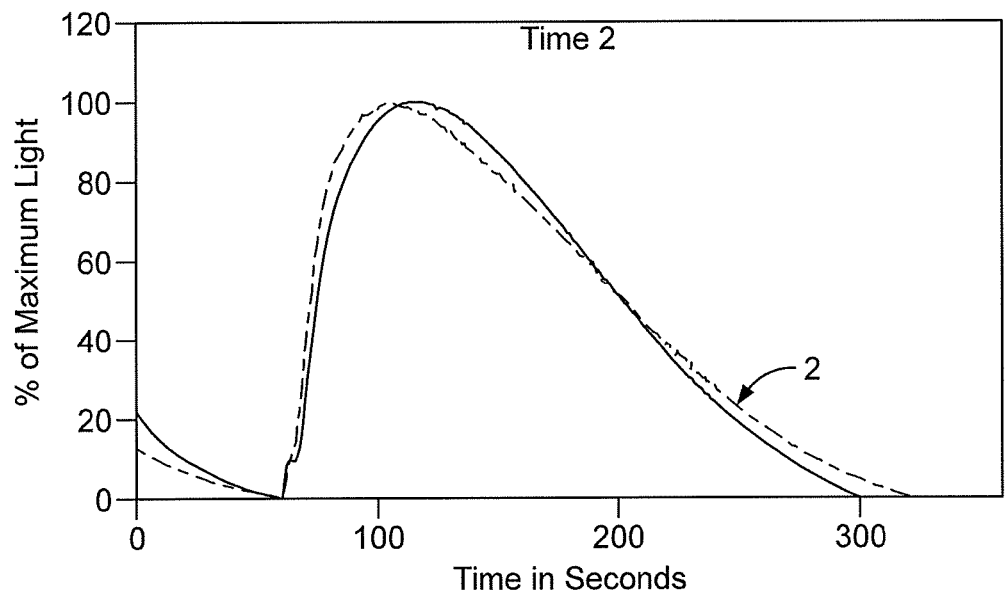
FIG. 13B shows a light emission curve obtained for a sample from Individual VII taken 1 hour after administration of a 4-component formulation as described in Example 3.
Figure 13C:
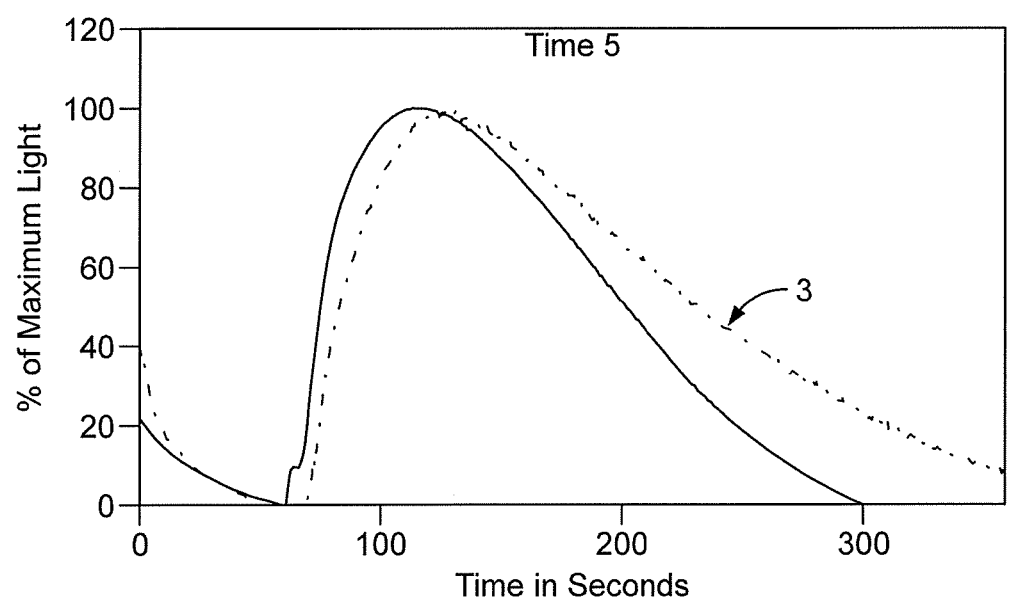
FIG. 13C shows a light emission curve obtained for a sample from Individual VII taken 3 hours after the sample for FIG. 13B was taken.

An individual VII claimed to be feeling stressed and tired. The light emission curve produced using a blood sample provided by the individual (see FIG. 13A; 1) had a shape similar to Reference shape code F (see Explanations, 1 Light emission curves, and FIG. 1B) suggesting stress and fatigue (depressed response), with the signal low. The formulation as described above in Example 3 was administered to the individual in a capsule and one hour after this administration the individual provided another blood sample which produced the light emission curve 2 as shown in FIG. 13B. The curve 2 indicates a notable right shift to the curve (compared to FIG. 13A; 1), with the response being above the upper limit of the normal range. After a further 3 hours, another blood sample was taken and the light emission curve obtained for this (FIG. 13C; 3) showed a signal within the normal range. The curve 3, which is slightly displaced because of a delay in injecting the fMLP, has shifted significantly to the right.

Example 11

An individual VIII reported feeling ill on 6 Oct. 2016. A blood sample provided on that day by the individual was subjected to testing in accordance with the procedure described in Example 4. The light emission curve (FIG. 14, curve B), produced using this sample, showed an increased response compared to the reference curve (FIG. 14, curve A) relating to a normal, healthy human. In view of the symptoms presented, an antibiotic was administered to the individual on 6 Oct. 2016. A blood sample provided one week later (13 Oct. 2016) was tested and the light emission curve (FIG. 14, curve C) produced using this sample showed a yet further heightened response. Light emission curves (FIGS. 14, D and E) produced using blood samples provided on 20th and 27 Oct. 2016, respectively, showed a gradual decrease in response and the individual reported that he felt well on 27 Oct. 2016. The individual reported that he felt unwell again on 3 Nov. 2016. The light emission curve (FIG. 14, curve F), produced using a blood sample provided on that day, shows an intense response; the curve shape being abnormal compared to reference curve A. The formulation described in Example 3 was administered to the individual on 3 Nov. 2016 in capsule form and, again, once weekly on 10th, 17th and 24 Nov. 2016. Curves (G, H and I, respectively) produced using blood samples provided on those days show a gradually decreased response. One week later (1 Dec. 2016), the individual reported feeling well and the light response curve (FIG. 14, curve J), produced using a blood sample provided on that day, shows a further lowered response. On 8 Dec. 2016, although the individual still reported feeling well, a blood sample taken that day produced a light emission curve (FIG. 14, curve K) showing a response which is heightened and just above the normal range, although having a shape approaching that of reference curve A. Possible reasons for this heightened response include the possibility that the individual had undertaken exercise before providing the blood sample and the possibility that, despite the fact that he felt well, the individual was pre-symptomatically suffering from another infection. This latter possibility was not, however, reported subsequently by the individual.

Figure 14:
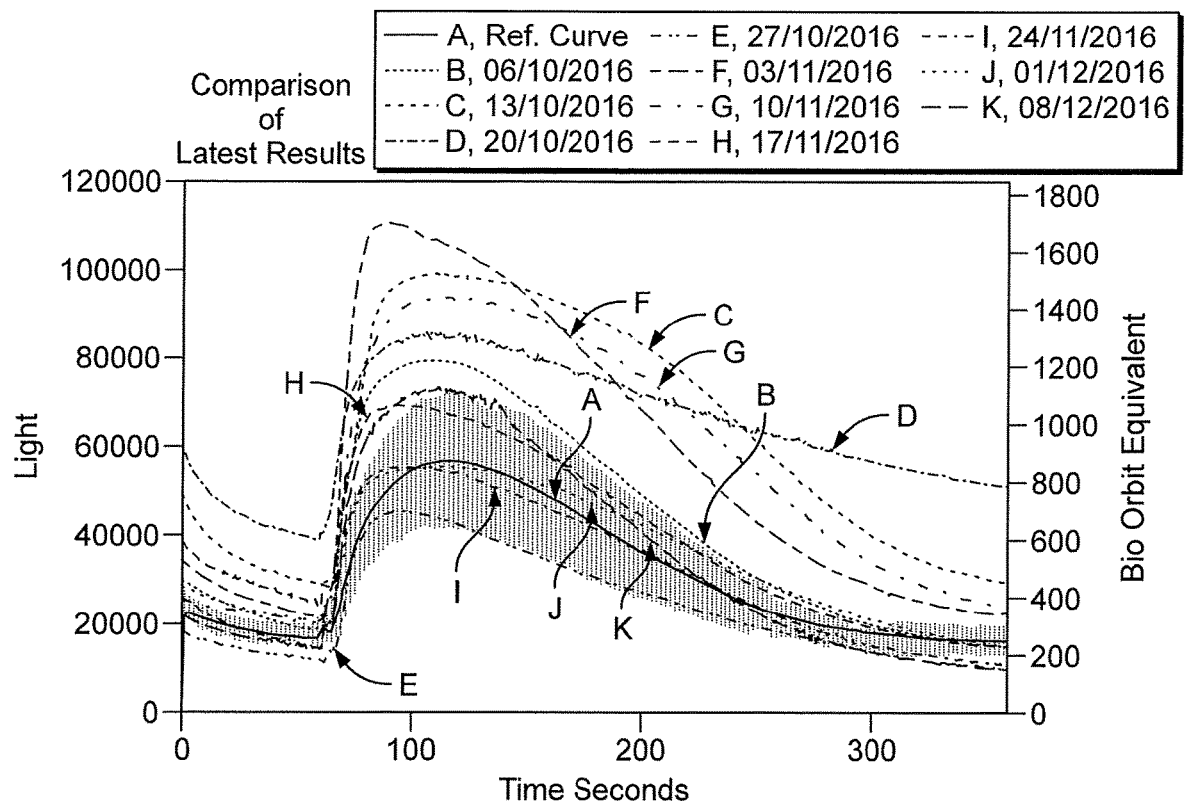
FIG. 14 shows a light emission curve obtained for a sample from Individual VIII taken that was subjected to testing in accordance with example 4.
Figure 15:
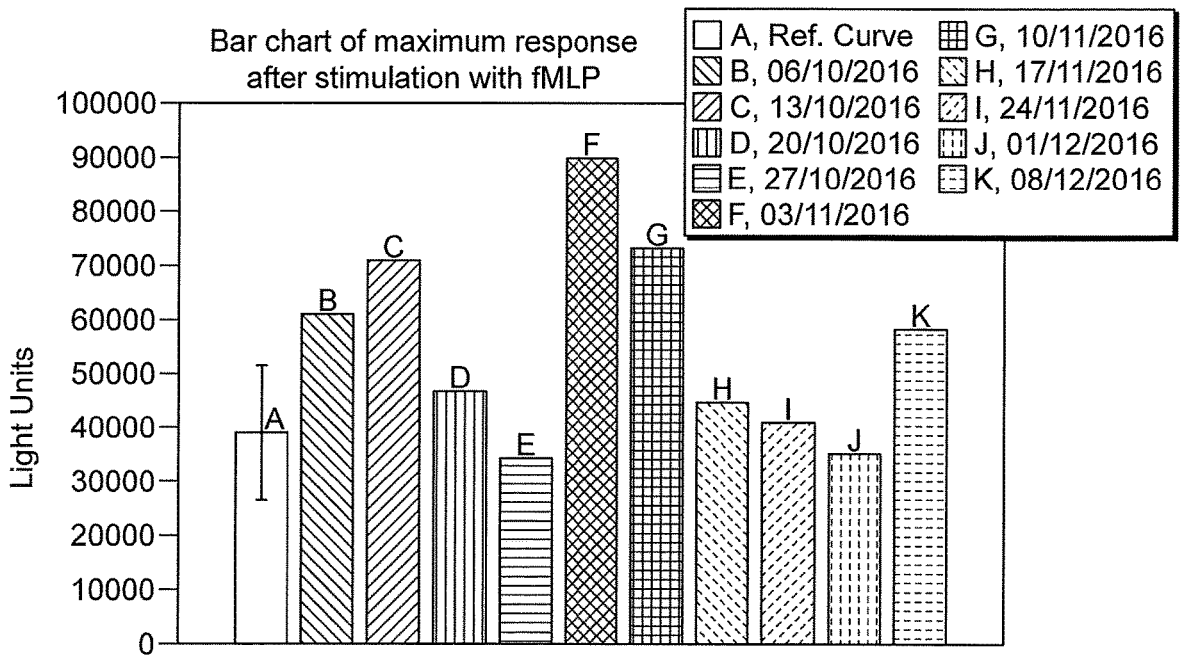
FIG. 15 shows a bar chart illustrating the maximum light emission responses according to the curves shown in FIG. 14.

FIG. 15 is a bar chart showing the maximum light emission responses according to the curves A to K shown in FIG. 14.

Example 12

A trial was carried out at a stable that trains horses mainly for jump racing (National Hunt horses). With over 100 horses in residence at any one time, it was very easy for the assistant manager at the stable to find pairs of horses that were matched for age and sex and which had viral respiratory infections characterised by similar symptoms and of approximately the same duration. Some of these symptoms were serious discharge (runny nose), often accompanied by cough and possibly fever. For this trial, horses were excluded with more advanced symptoms which had progressed deeper into the lungs and had developed into secondary bacterial infections. All the horses selected for this trial, because of their respiratory infections, had their training for entry into competition races suspended. Five pairs of horses were selected for the trial.

In each pair of horses, one was arbitrarily picked as the treatment horse and the other as the non-treatment control. Each treatment horse was given an initial dose of the formulation described in Example 3. The dose was made by mixing 2 g of the formulation with 30 mL of water in a 50 mL screw top, polypropylene centrifuge tube. The tube was gently inverted at least 5 times to dissolve/disperse the powder gently without vigorous shaking. The entire contents of the tube were taken up into a 50 mL dosing syringe and delivered down the back of the throat of the horse to enter the stomach directly. The treatment horses were dosed three times a day in the first two days of the trial and twice a day for 4 more days.

Results:

The treatment horses all responded to the treatment described above. The horses with less intense symptoms showed good improvement, compared to their non-treatment control, within 24 hours. It took 48 hours for the horses with more severe symptoms to start to show improvement. The symptoms of the infection in the control horses all worsened compared to the treatment horses. In one case, within 36 hours the treatment horse was taken for a ride by his trainer while its non-treatment control was in a corner in his stable looking very unhappy. Within 5 days, all the treatment horses were well enough to ride. The three of the non-treatment controls eventually recovered after 3 weeks with the other 2 non-treatment controls developing symptoms suggestive of a secondary bacterial infection and were treated by the stable vet.

Example 13

A senior vet who looks after very many racing camels used the formulation described in Example 3 on two separate occasions, with 5 sick camels each time. The method used to dose the camels was similar to that used for horses in which 2.0-2.2 g of the formulation was mixed with 30 ml of water and taken up into a 50 ml dosing syringe. The liquid was dispensed from the dosing syringe onto the mucosa of the mouth of the camels so that it is taken up directly into the bloodstream. Camels are pseudo ruminants and dispensing the dose directly into the rumen would have delayed it getting in the blood, possibly for days. Also, it would not have been possible to compare treatment from one camel to another. The procedure used, which is called flush to the mouth, is generally used to deliver medication to camels. The vet reported after the first trial that he got a good response, particularly from animals with cold- and flu-like symptoms. He reported that treated camels recovered in less than a week, while non-treated camels recovered in 10 to 15 days.

On the second occasion, the vet started with a 2.2 g dose, 3 times a day, of the formulation which was administered to the sick camels as described above. Within 24 hours, he reported that the camels' coughs had ceased and their runny noses had dried up in the immediate days following. The camels were fully recovered and deemed fit and well to race the next week.

Example 14

Figure 17:
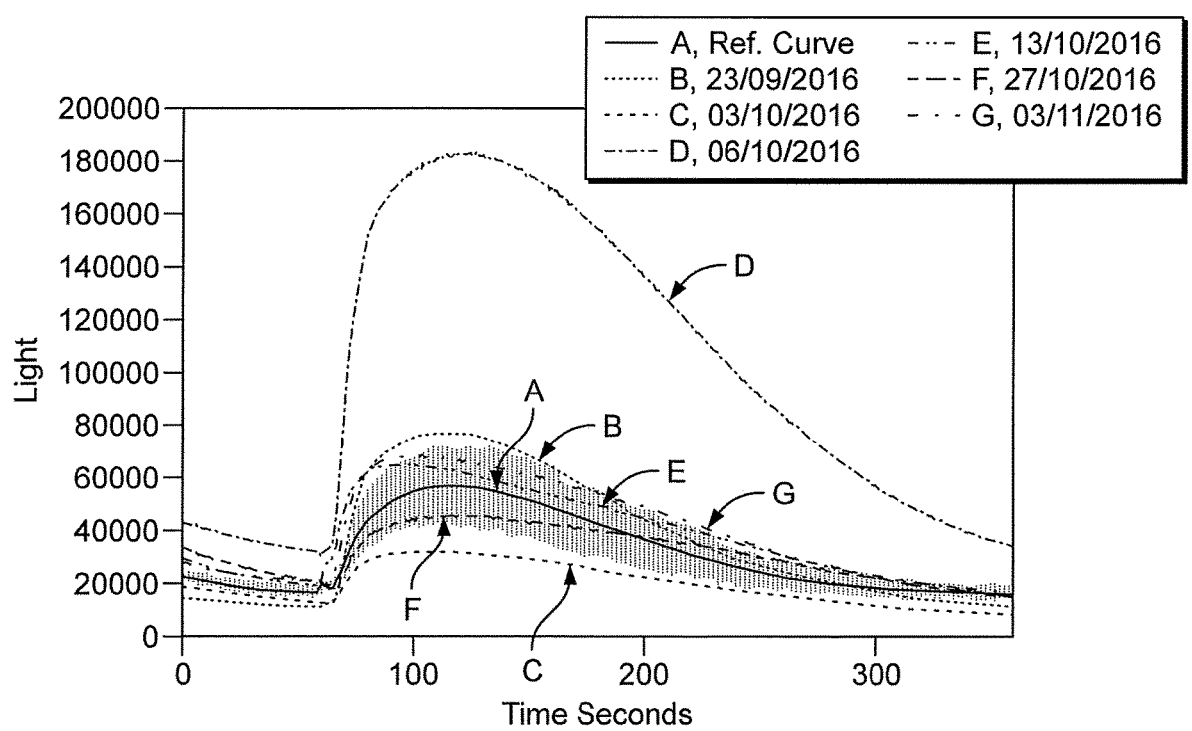
FIG. 17 shows various light emissions curves obtained for samples taken from an athlete that had initially reported being frequently fatigued with symptoms of a respiratory infection.

An athlete reported that he had been frequently fatigued and had symptoms of a respiratory infection on 23 Sep. 2016. A light emission curve (FIG. 17, curve B) was produced using a blood sample provided on that day. He took the formulation described in Example 3, in capsule form, after testing on 23 Sep. 2016. The infection improved, as indicated by how he felt and by the light emission curve C produced using a blood sample provided on 3 Oct. 2016. On 6 Oct. 2016, the athlete complained of feeling fatigued. The light emission curve D, produced using a blood sample provided on that day, showed a strong infection suggested by the shape, very high signal and a later time to peak, to be a probable bacterial infection. Treatment with an appropriate antibiotic led to improvement in the athlete's symptoms which are indicated in the subsequent test results (curves E, F, G and H).

The invention claimed is:

1. A tablet or capsule consisting essentially of 30%-45% by weight grapeseed extract, 30%-45% by weight green tea extract, 5%-20% by weight pine bark extract, and 5%-20% by weight pomegranate extract.

2. The tablet or capsule of claim 1, consisting essentially of 35% to 45% by weight grapeseed extract, 30% to 40% by weight green tea extract, 5% to 15% by weight pine bark extract and 5% to 15% by weight pomegranate extract.

3. The tablet or capsule of claim 1, consisting essentially of 37% to 42% by weight grapeseed extract, 32% to 37% by weight green tea extract, 7% to 15% by weight pine bark extract and 7% to 15% by weight pomegranate extract.

* * * * *